United States Patent
Wong

(10) Patent No.: US 9,283,405 B2
(45) Date of Patent: Mar. 15, 2016

(54) METHOD FOR REAL-TIME QUALITY ASSURANCE ASSESSMENT OF GANTRY ROTATION AND COLLIMATOR ROTATION IN RADIATION THERAPY

(71) Applicant: The Johns Hopkins University, Baltimore, MD (US)

(72) Inventor: John Wai-Chiu Wong, Ruxton, MD (US)

(73) Assignee: The Johns Hopkins University, Baltimore, MD (US)

( * ) Notice: Subject to any disclaimer, the term of this patent is extended or adjusted under 35 U.S.C. 154(b) by 36 days.

(21) Appl. No.: 14/449,349

(22) Filed: Aug. 1, 2014

(65) Prior Publication Data
US 2015/0036806 A1  Feb. 5, 2015

Related U.S. Application Data

(60) Provisional application No. 61/861,612, filed on Aug. 2, 2013.

(51) Int. Cl.
*A61N 5/10* (2006.01)
(52) U.S. Cl.
CPC .................................... *A61N 5/1075* (2013.01)
(58) Field of Classification Search
CPC . A61N 5/1075; A61N 5/1071; A61N 5/1049; A61N 2005/1061; A61N 5/1048; A61N 5/1067; A61N 2005/1076; A61N 2005/1059; A61N 5/1037; A61N 2005/1051; A61N 2005/1052; A61N 5/1039; A61N 5/1042; A61N 5/1084; A61N 2005/105; A61N 2005/1056; A61N 2005/1054; A61N 2005/106; A61B 6/583; A61B 6/5276; A61B 5/0035; A61B 5/0046; A61B 5/0555; A61B 6/032; A61B 6/0457; A61B 6/145; A61B 6/4417; A61B 6/482; A61B 6/5247; A61B 6/584; A61B 6/585; A61B 6/586; G09B 23/286
USPC .............................................. 378/62, 65, 209
See application file for complete search history.

(56) References Cited

U.S. PATENT DOCUMENTS 4,995,068 A   2/1991 Chou et al.
6,842,502 B2  1/2005 Jaffray et al.
(Continued)

FOREIGN PATENT DOCUMENTS

WO   2009091382 A8   7/2009
WO   2011005862 A2   1/2011

OTHER PUBLICATIONS

International Search Report and the Written Opinion of the International Searching Authority dated Jun. 4, 2013 for application PCT/US2013/029775.

*Primary Examiner* — Irakli Kiknadze
(74) *Attorney, Agent, or Firm* — JHU Technology Ventures

(57) ABSTRACT

A method and device for real-time mechanical and dosimetric quality assurance measurements in radiation therapy provides a unified measurement of mechanical motion and radiation components of the machine. The device includes an imaging surface for receiving multiple energy sources. The imaging surface has an imaging plane positioned on a same plane as an isocenter of a medical accelerator. A camera measures and records data related to the multiple energy sources. A mirror system can be used to direct the multiple energy sources to the camera for further processing. However, in some instances the mirror system may not be necessary. The device can also include computer control in order to automate the movement of the device and/or automation of the QA protocol. The device can also be used in executing a method for assessing gantry and collimator rotation.

14 Claims, 39 Drawing Sheets

(56) References Cited

U.S. PATENT DOCUMENTS

| | | |
|---|---|---|
| 7,789,561 B2 | 9/2010 | Wu et al. |
| 8,948,842 B2 * | 2/2015 | Raleigh ............ A61B 5/0037 382/131 |
| 2003/0007601 A1 | 1/2003 | Jaffray et al. |
| 2003/0076926 A1 | 4/2003 | Renner |
| 2003/0083564 A1 | 5/2003 | Ghelmansarai et al. |
| 2005/0013406 A1 | 1/2005 | Dyk et al. |
| 2009/0067576 A1 | 3/2009 | Maltz |
| 2012/0168630 A1 | 7/2012 | Beddar et al. |
| 2013/0267829 A1 * | 10/2013 | Ojha ............ A61B 6/032 600/411 |
| 2014/0016759 A1 * | 1/2014 | Ngar ............ A61N 5/1075 378/207 |
| 2014/0350387 A1 * | 11/2014 | Siewerdsen ........ G01R 33/028 600/424 |

* cited by examiner

QA TASKS PER MACHINE - CRITICAL YET TIME CONSUMING

| DAILY (10 MINUTES) | MONTHLY (5 HOURS) | ANNUAL (4 DAYS) |
|---|---|---|
| LASER LOCALIZATION | LOCALIZING LASERS | COLLIMATOR ROTATION ISOCENTER |
| DISTANCE INDICATOR | LIGHT/RADIATION FIELD COINCIDENCE | GANTRY ROTATION ISOCENTER |
| COLLIMATOR SIZE INDICATOR | LIGHT/RADIATION FIELD ASYMMETRIC | ELECTRON APPLICATOR INTERLOCKS |
| X-RAY OUTPUT CONSTANCY | DISTANCE CHECK DEVICE FOR LASERS | COINCIDENCE OF RADIATION AND MECHANICAL ISOCENTER |
|  | COMPARED WITH FRONT POINTER | TABLE TOP SAG/TABLE ANGLE |
| X-RAY OUTPUT CONSTANCY | GANTRY/COLLIMATOR ANGLE INDICATORS | TABLE TRAVEL MAXIMUM RANGE ....... |
| ELECTRON OUTPUT CONSTANCY | ACCESSORY TRAYS |  |
|  | JAW POSITION INDICATORS ASYMMETRIC | X-RAY FLATNESS CHANGE |
|  | CROSS HAIR CENTERING | X-RAY SYMMETRY |
|  | TREATMENT COUCH POSITION INDICATORS | ELECTRON FLATNESS CHANGE |
|  |  | ELECTRON SYMMETRY CHANGE |
|  | WEDGE PLACEMENT ACCURACY | SRS ARC ROTATION MODE |
|  | COMPENSATOR PLACEMENT ACCURACY | X-RAY/ELECTRON OUTPUT CALIBRATION |
|  | X-RAY OUTPUT CONSTANCY | SPOT CHECK OF FIELD SIZE AND DEPENDENT |
|  | ELECTRON OUTPUT CONSTANCY | OUTPUT FACTOR FOR X-RAY |
|  | TYPICAL DOSE RATE OUTPUT CONSTANCY | OUTPUT FACTORS FOR ELECTRON APPLICATORS |
|  | PHOTON BEAM PROFILE CONSTANCY | X-RAY BEAM QUALITY |
|  | ELECTRON BEAM PROFILE CONSTANCY | ELECTRON BEAM QUALITY |
|  | ELECTRON BEAM ENERGY CONSTANCY | PHYSICAL WEDGE |
|  | BACKUP MONITOR CHAMBER CONSTANCY | X-RAY MONITOR UNIT |
|  |  | X-RAY OUTPUT CONSTANCY VS DOSE RATE |
|  |  | X-RAY OUTPUT CONSTANCY VS GANTRY ANGLE |
|  |  | ELECTRON AND X-RAY OFF-AXIS FACTOR |
|  |  | ARC MODE (EXPECTED MU DEGREES) |
|  |  | TBI/TSET OUTPUT CALIBRATION |
|  |  | TBI/TSET ACCESSORIES |
|  |  | BEAM ENERGY CONSTANCY, |

PHYSICIST MAKES 5,300 QA MEASUREMENTS PER MACHINE/YEAR

CURRENTLY MEASURED WITH DIFFERENT DEVICES

FIG. 1

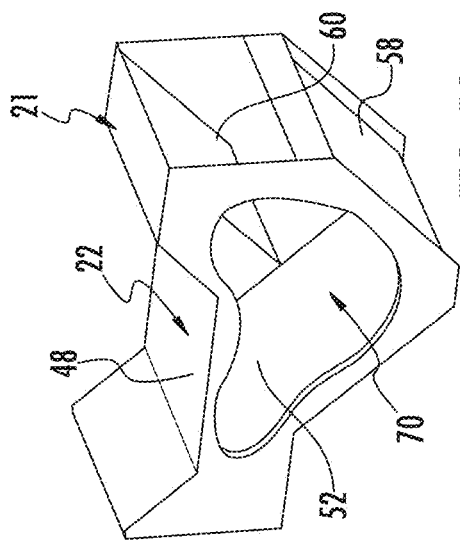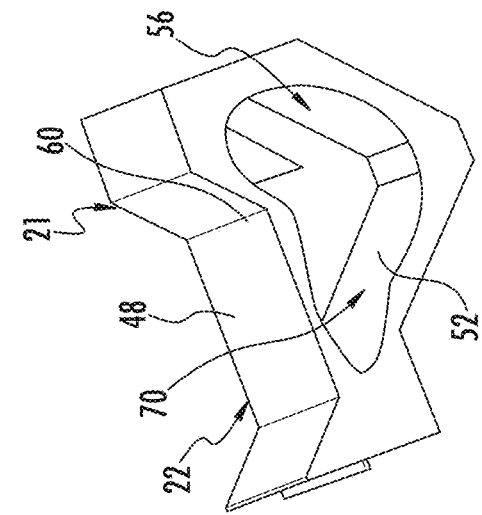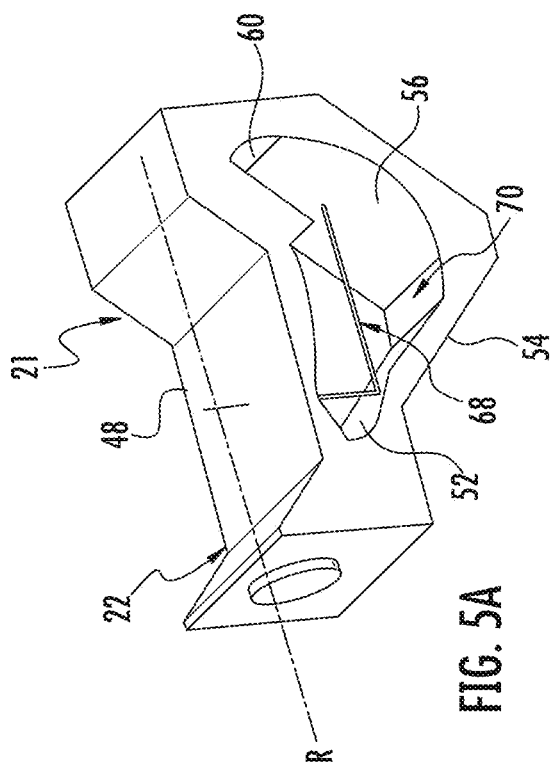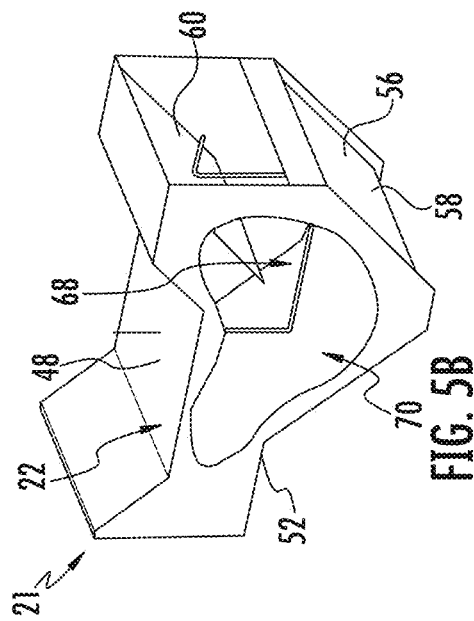

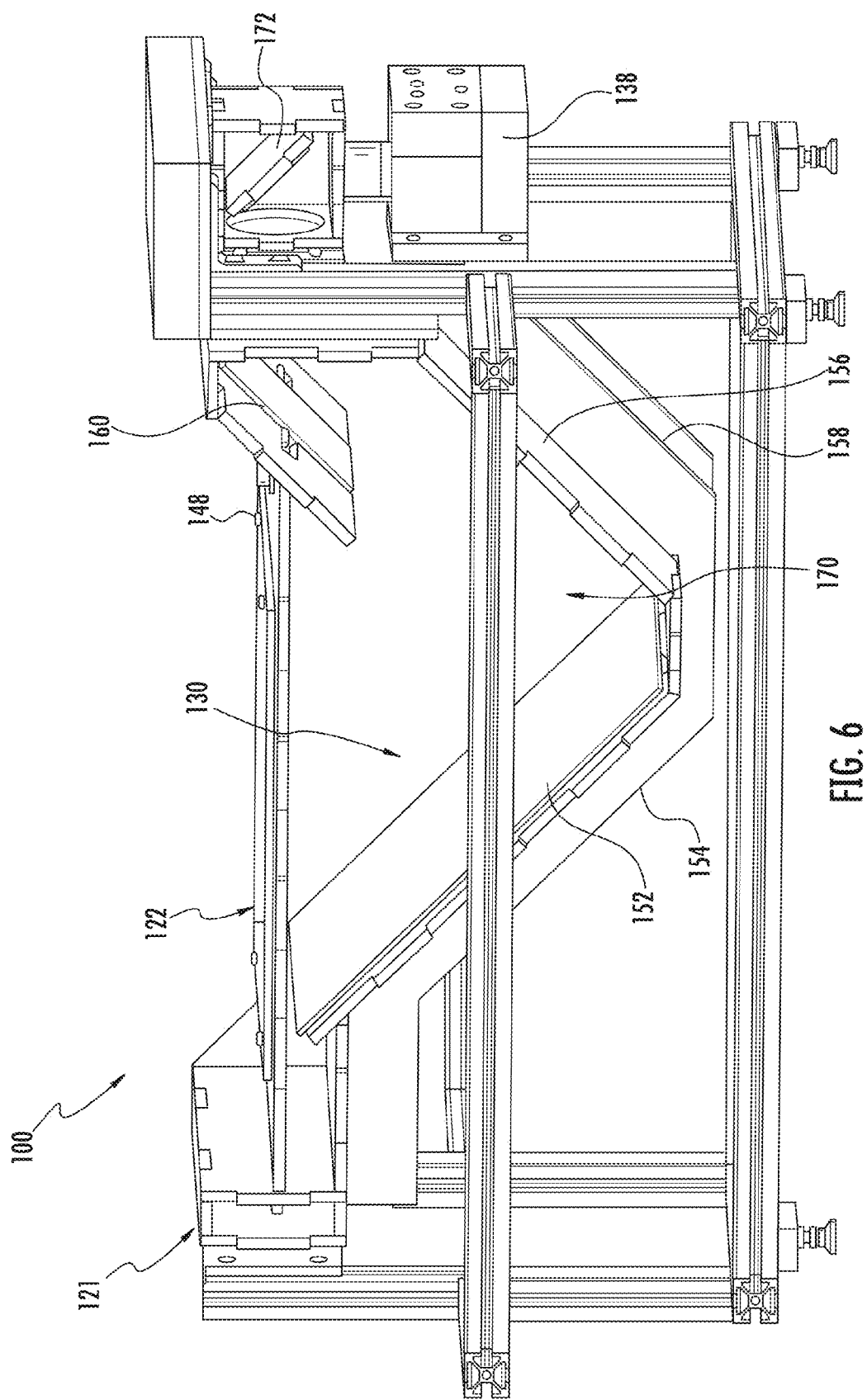

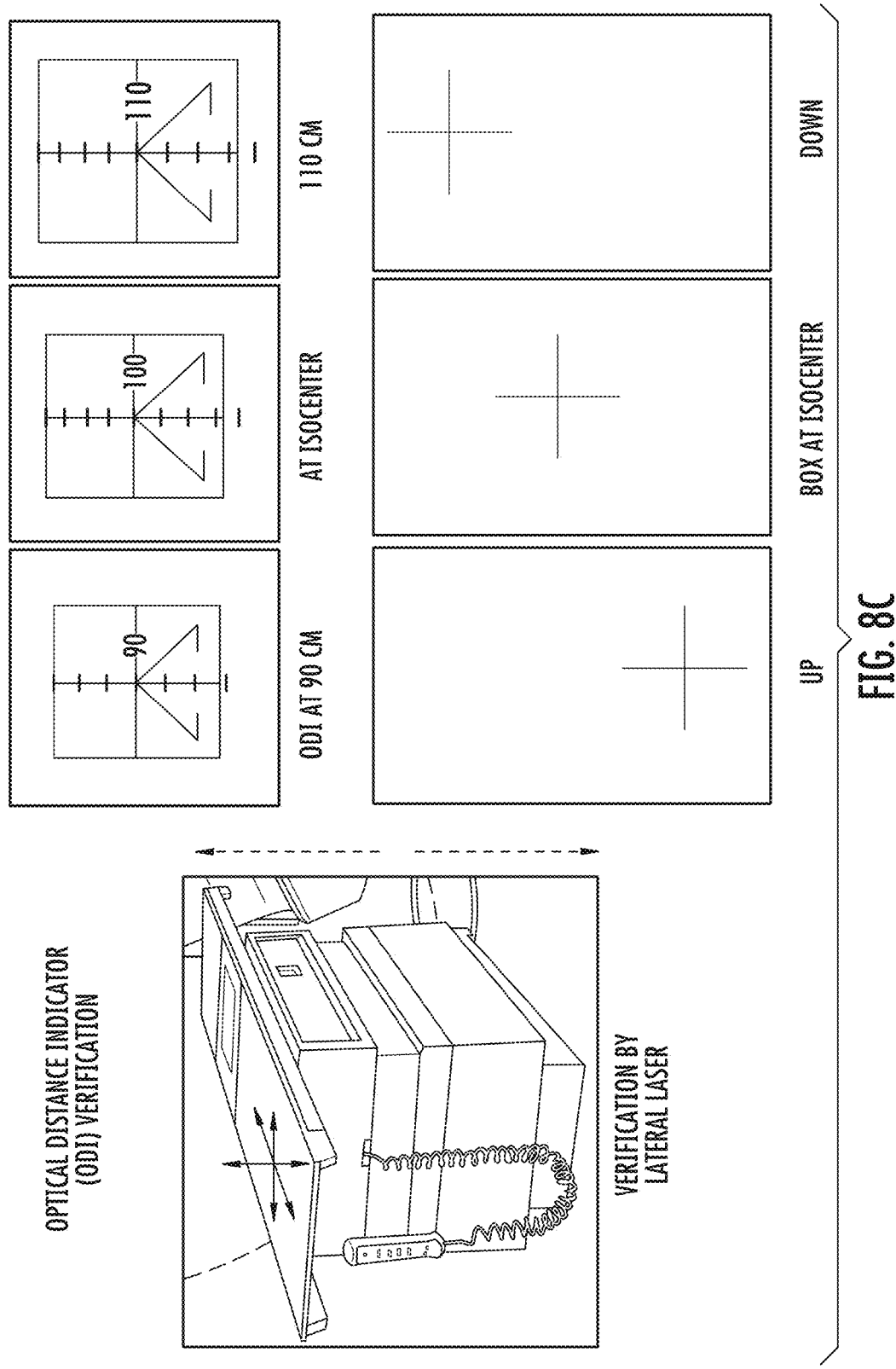

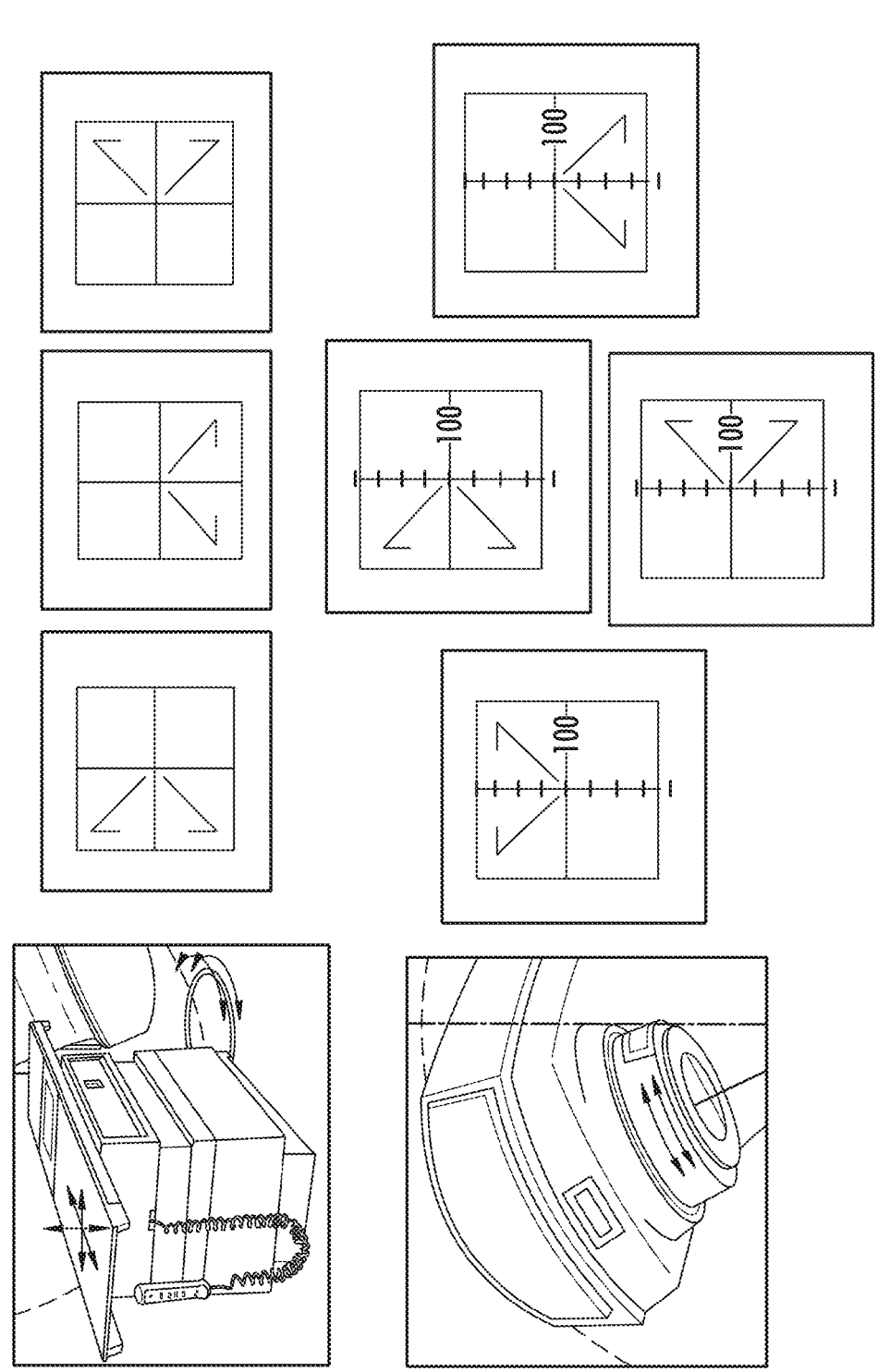

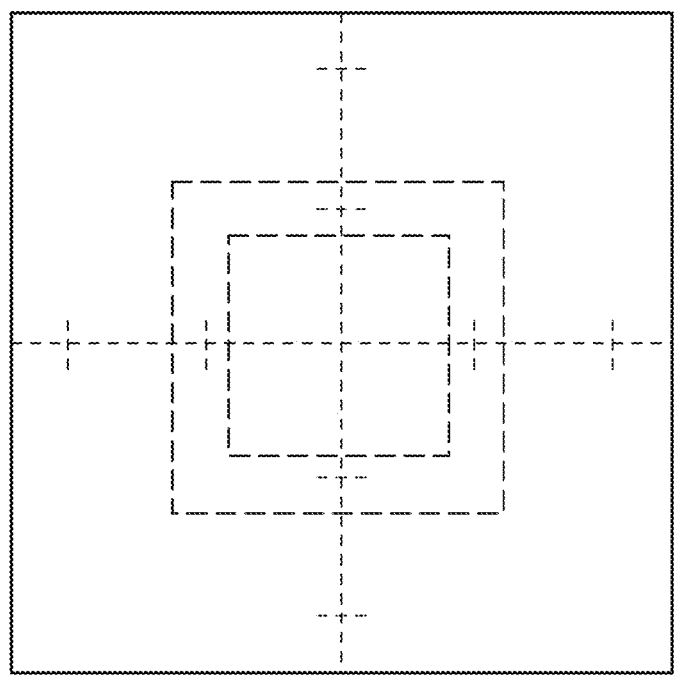
FIG. 9
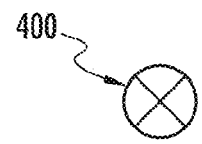
FIG. 10
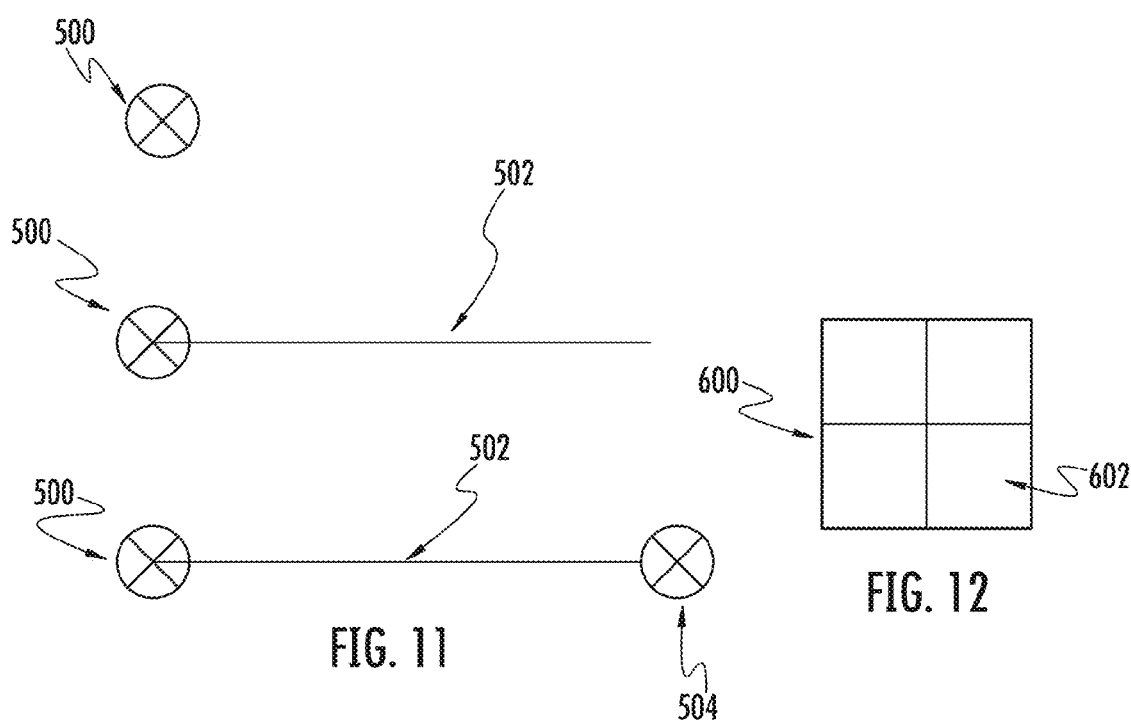
FIG. 11
FIG. 12

METHOD FOR REAL-TIME QUALITY ASSURANCE ASSESSMENT OF GANTRY ROTATION AND COLLIMATOR ROTATION IN RADIATION THERAPY

CROSS REFERENCE TO RELATED APPLICATION

This application claims the benefit of U.S. Provisional Patent Application No. 61/861,612 filed on Aug. 2, 2013, which is incorporated by reference, herein, in its entirety.

FIELD OF THE INVENTION

The present invention relates generally to radiation therapy. More particularly the present invention relates to quality assurance assessment of gantry rotation and collimator rotation in radiation therapy.

BACKGROUND OF THE INVENTION

Medical accelerators are used for radiation treatment of cancer patients and emit radiation in 360°. A patient lies on a platform, while a head of the device is rotated around the body of the patient. Quality assurance (QA) of the integrity of the medical accelerators is paramount to ensure the safe delivery of radiation treatment. The two main criteria used for QA is radiation reproducibility and mechanical integrity of the machine. The QA tasks specifically consist of quantifying the accuracy and precision of mechanical motions of the accelerators, various optical indicators, and the delivered dosimetry. FIG. 1 illustrates a chart of QA tasks per medical accelerator that must be performed daily, monthly, and annually.

FIG. 2 illustrates a front view of a medical accelerator used for radiation treatment. As illustrated in FIG. 2, one task of QA is to ensure that radiation beams along an axis and the positioning aids, in the form of laser beams, align at an isocenter of the medical accelerator. QA of this alignment is important in order to verify that the radiation beams along axis 1 are configured to treat the patient accurately without causing burns or other undesired side effects.

At present, almost all of the QA tasks listed in FIG. 1 are performed with different apparatus. The mechanical and optical components are examined visually, where the data is not amenable to documentation. For example, a technician checks the light source by directing the source onto the patient couch, and rotating it to make sure it moves about the isocenter of the medical accelerator. The dosimetry is measured with a variety of ionization detectors with the two-dimensional array of discrete detectors being most popular. Higher resolution measurements are measured with films where the data conversion process can be tedious. Some of these tasks are performed on a daily, monthly or yearly basis, and can take hours to perform. For example, while daily maintenance only takes approximately 10 minutes, a monthly maintenance of such machines to test the output and the mechanical integrity of the machine typically will take between 5-6 hours, the results of the testing partially documented. In fact, annual maintenance on the machine can take approximately 4 days to complete.

Currently, to assess integrity of collimator rotation, a piece of film is placed flat on the couch at the plane of the isocenter. A long slit beam of narrow width is set up, such as a slit of approximately 0.1 to 1 cm×20 cm. The piece of film is exposed with the collimator rotated at different angles. Alternately, with the collimator fixed, the table can be rotated at different angles. The film is developed after several different angles are shot to determine, visually or digitally, the dimension of the circle that encompasses all of the intersections of horizontal rays. This gives a measure of the isocenter integrity of collimator rotation. The resultant film is often referred to as a star-shot image.

The current method to assess the integrity of gantry rotation includes sandwiching a vertical film between two blocks of plastic. The sandwich of blocks and film is placed vertically in the plane of gantry rotation. A long slit beam is set up with the narrow width orthogonal to the vertical film. The gantry is rotated 360° around the vertical film block exposing the film at different gantry angles. After several different angles are shot, the film is developed. The dimension of the circle that encompasses all of the intersections of the vertical rays is determined either visually or digitally. This gives a measure of the isocenter integrity of gantry rotation.

Accordingly, there is a need in the art for a device that provides a faster and more accurate measurement of collimator rotation and gantry rotation.

SUMMARY

According to a first aspect of the present invention a method for real-time mechanical and dosimetric quality assurance measurements in radiation therapy includes positioning a QA device at an isocenter of a medical accelerator. The method also includes setting up a small square radiation field and exposing the QA device to the small square radiation field at an angle of the collimator. Additionally, the method includes repeating the exposure to the small square radiation field is repeated for various collimator angles and determining a center of mass of all of the small square radiation fields imaged by the QA device to obtain a measure of the isocenter integrity of collimator rotation.

In accordance with an aspect of the present invention, a method for real-time mechanical and dosimetric quality assurance measurements in radiation therapy, includes positioning a QA device at an isocenter of a medical accelerator and setting up a small square radiation field. The method also includes exposing the QA device to the small square radiation field at an angle of the gantry and rotating the QA device. Additionally the method includes repeating the exposure to the small square radiation field and determining a center of mass of all of the small square radiation fields imaged by the QA device to obtain a measure of the isocenter integrity of gantry rotation.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIG. 1 illustrates a chart of QA tasks per medical accelerator that must be performed daily, monthly, and annually.

3D illustrates a perspective view of a device according to the features of the present invention sitting within the treatment range of a medical accelerator.

Figure 4A:
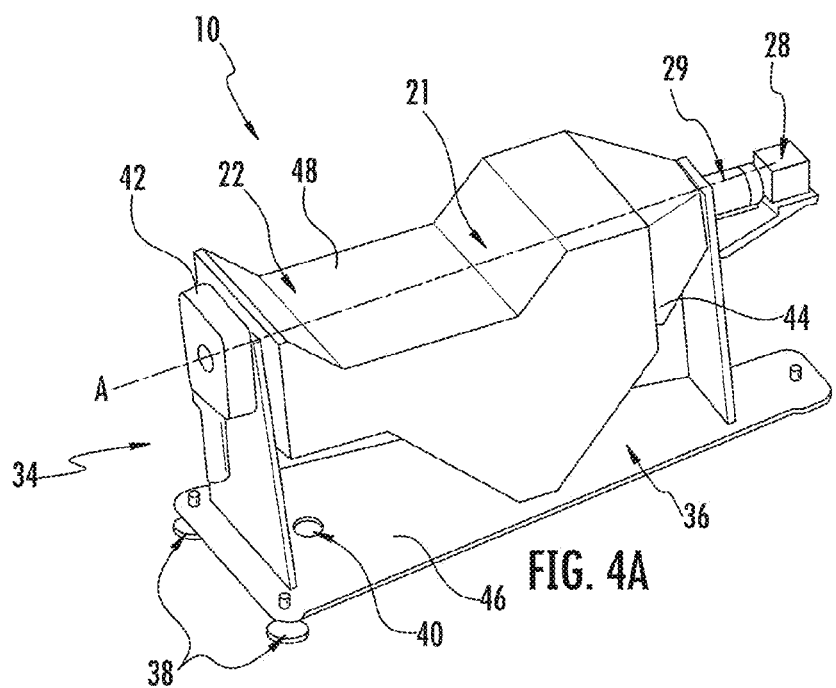
Figure 4B:
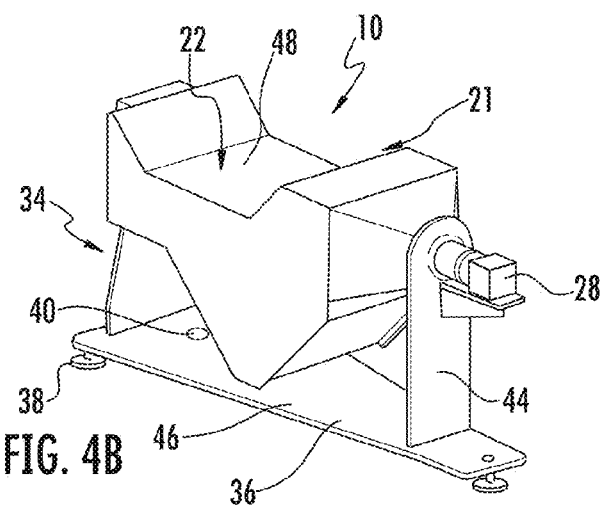
Figure 4C:
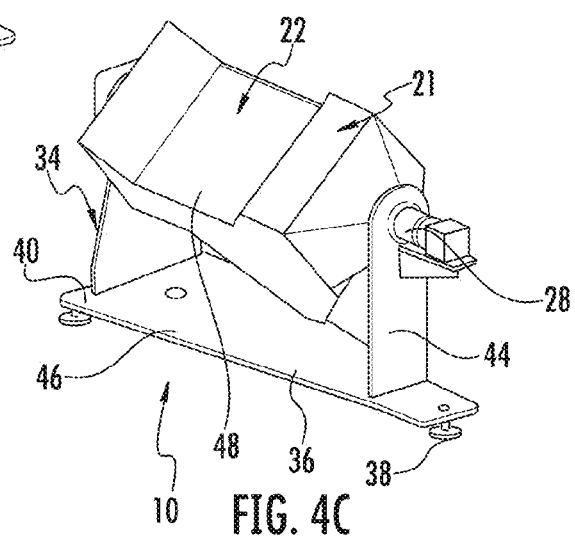

FIG. 4A illustrates a partially top-down perspective view of a device for real-time mechanical and dosimetric quality assurance measurements in radiation therapy according to the features of the present invention. FIG. 4B illustrates a perspective view of a device for real-time mechanical and dosimetric quality assurance measurements in radiation therapy according to the features of the present invention. FIG. 4C illustrates a perspective view of a rotated device for real-time mechanical and dosimetric quality assurance measurements in radiation therapy according to the features of the present invention.

FIG. 5A illustrates a partially sectional perspective view of a device for real-time mechanical and dosimetric quality assurance measurements in radiation therapy according to the features of the present invention. FIG. 5B illustrates a partially sectional perspective view of a device for real-time mechanical and dosimetric quality assurance measurements in radiation therapy according to the features of the present invention. FIG. 5C illustrates a partially sectional perspective view of a device for real-time mechanical and dosimetric quality assurance measurements in radiation therapy according to the features of the present invention. FIG. 5D illustrates a partially sectional perspective view of a device for real-time mechanical and dosimetric quality assurance measurements in radiation therapy according to the features of the present invention.

FIG. 6 illustrates a side view of a QA device according to an embodiment of the present invention.

Figure 7:
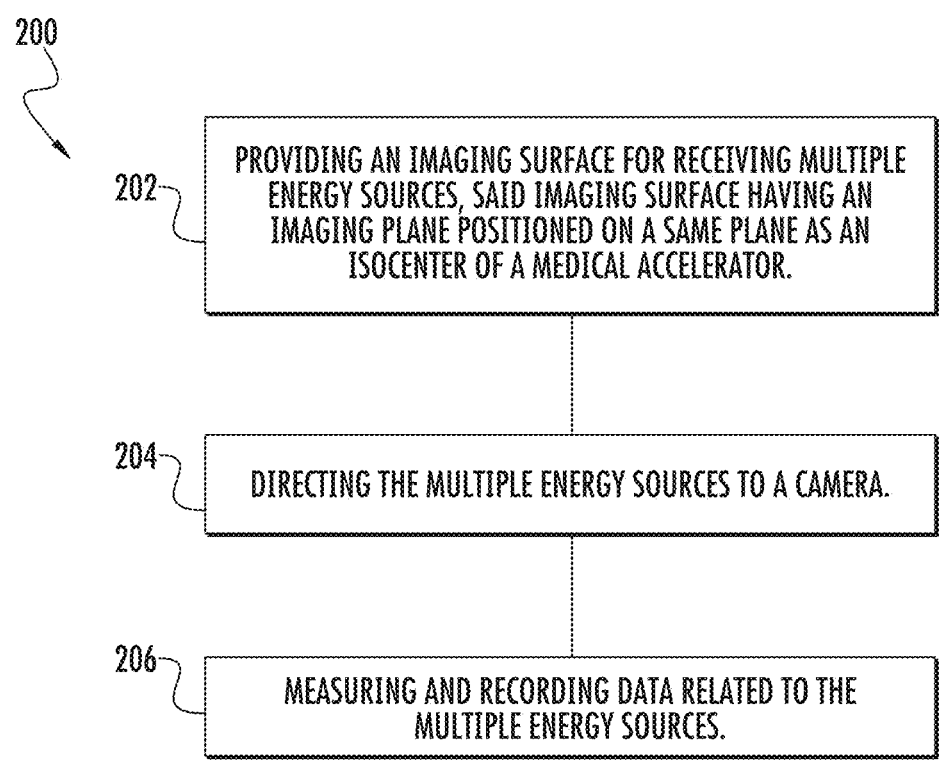

FIG. 7 illustrates a diagram of a method according to the features of the invention.

Figure 8A:
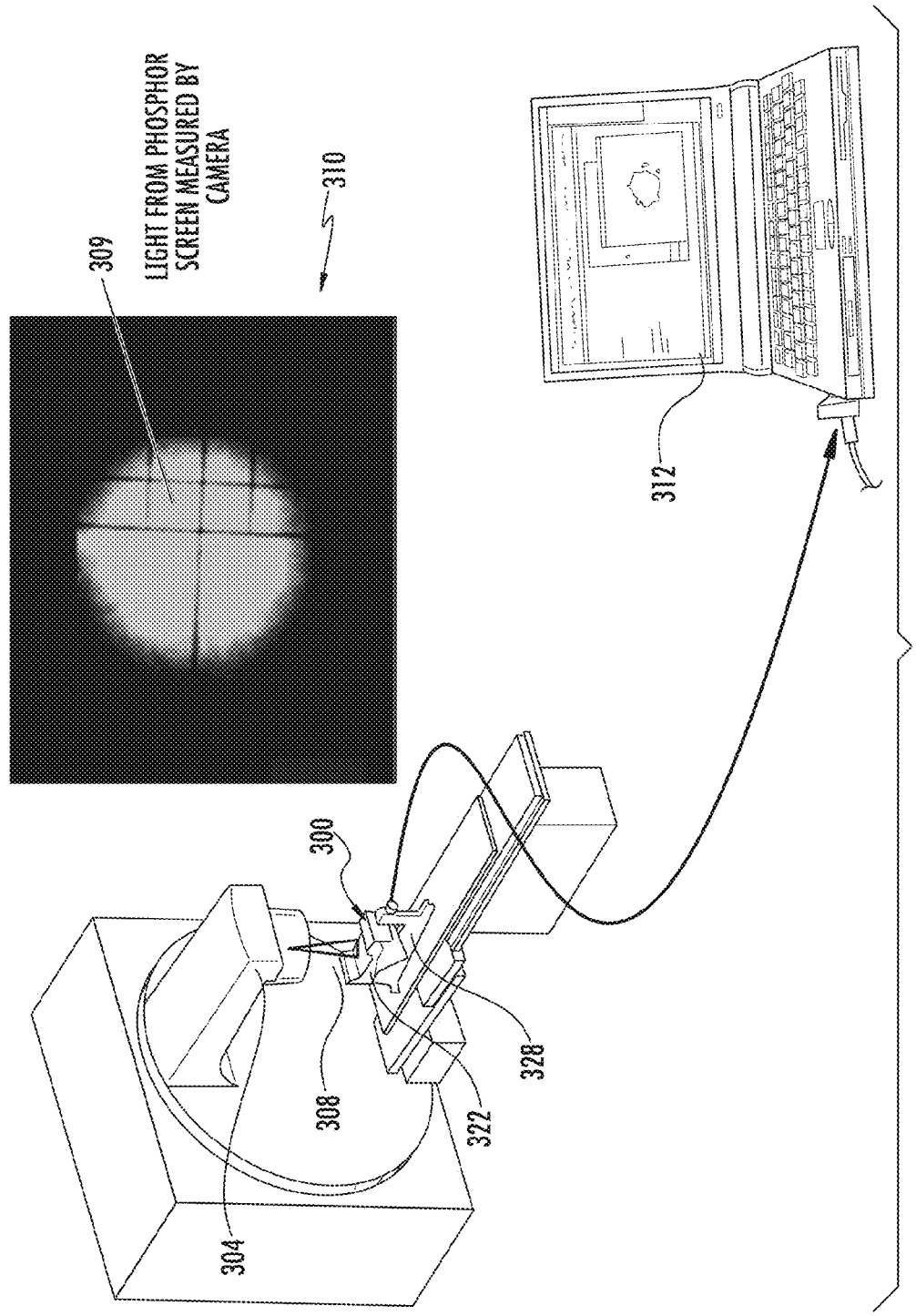
Figure 8B:
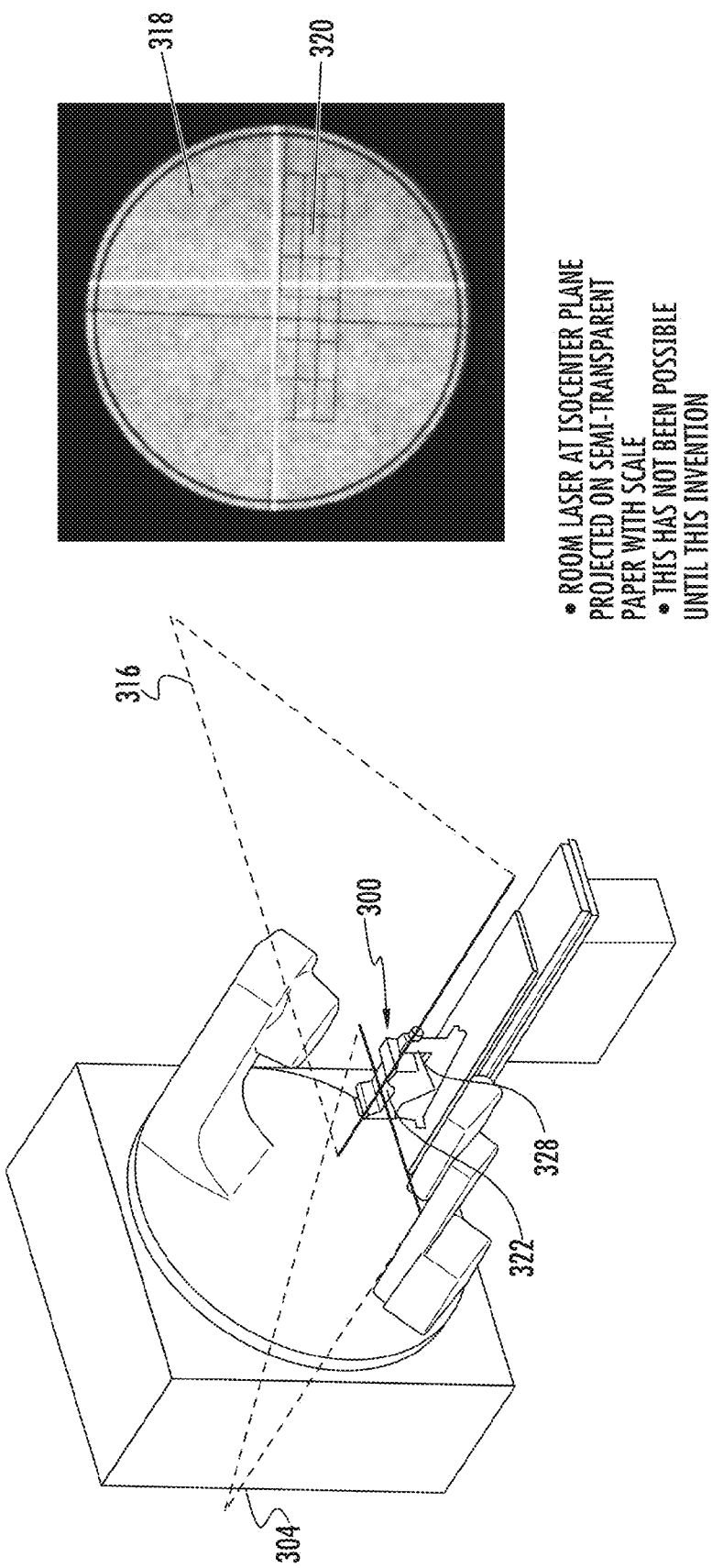

FIGS. 8A and 8B illustrate schematic diagrams showing a method according to the features of the invention. Note that the laser image has never been captured with prior art of QA devices.

FIG. 8C illustrates a method of performing table positioning QA, according to an embodiment of the present invention. Note that the light field image with the optical distant indicator has never been captured with prior art of QA devices.

FIG. 8D illustrates a method of performing rotation QA as captured optically for documentation, according to an embodiment of the present invention.

Figure 8E:
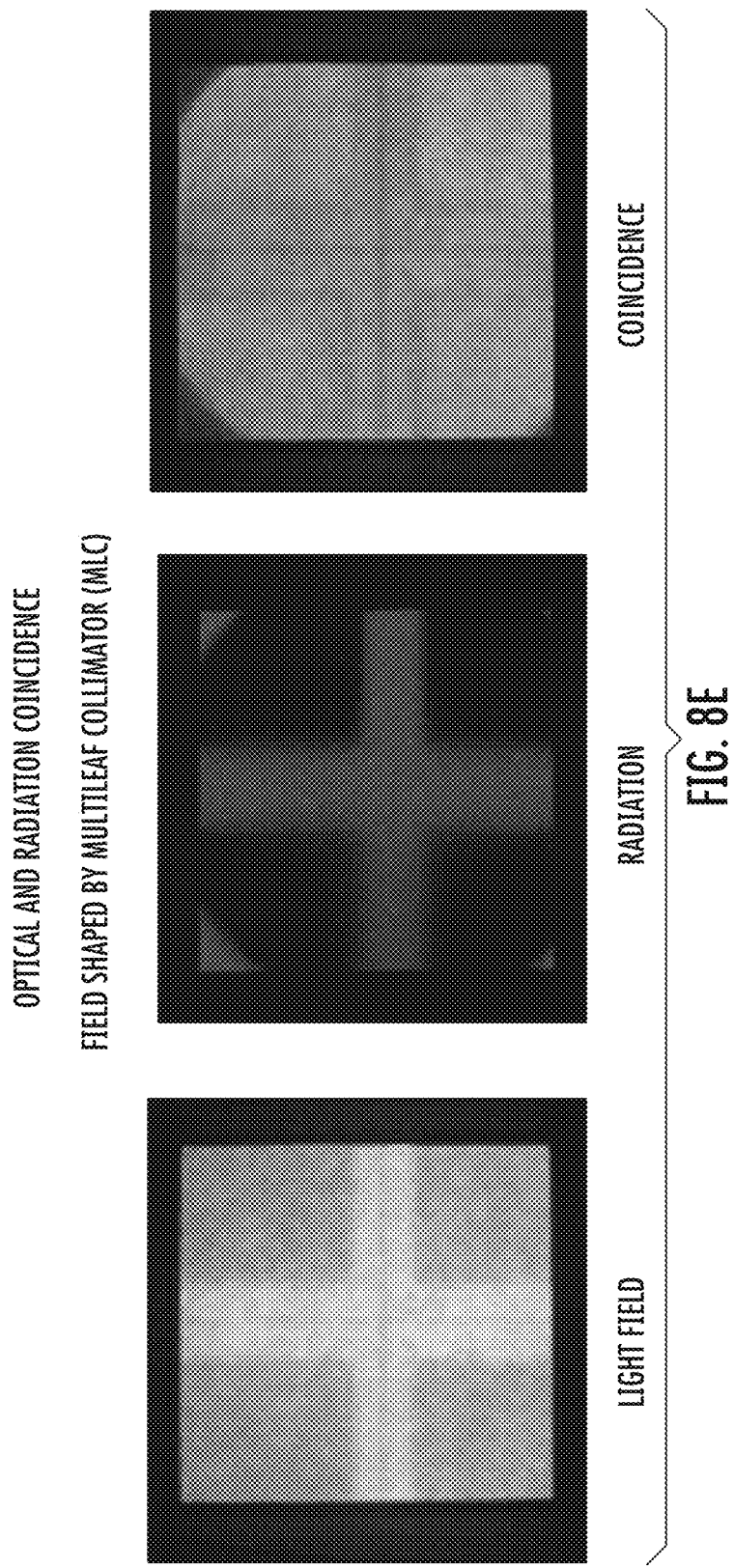

FIG. 8E illustrates a method of performing optical and radiation coincidence of a field shaped by the multi-leaf collimator.

FIG. 9 illustrates a hard coded digital image scale, according to an embodiment of the present invention.

FIG. 10 illustrates an analysis tool, provided by the software control program for the device of the present invention.

FIG. 11 illustrates a localization tool, provided by the software control program for the device of the present invention.

FIG. 12 illustrates a region of interest tool, provided by the software program for the device of the present invention.

Figure 13:
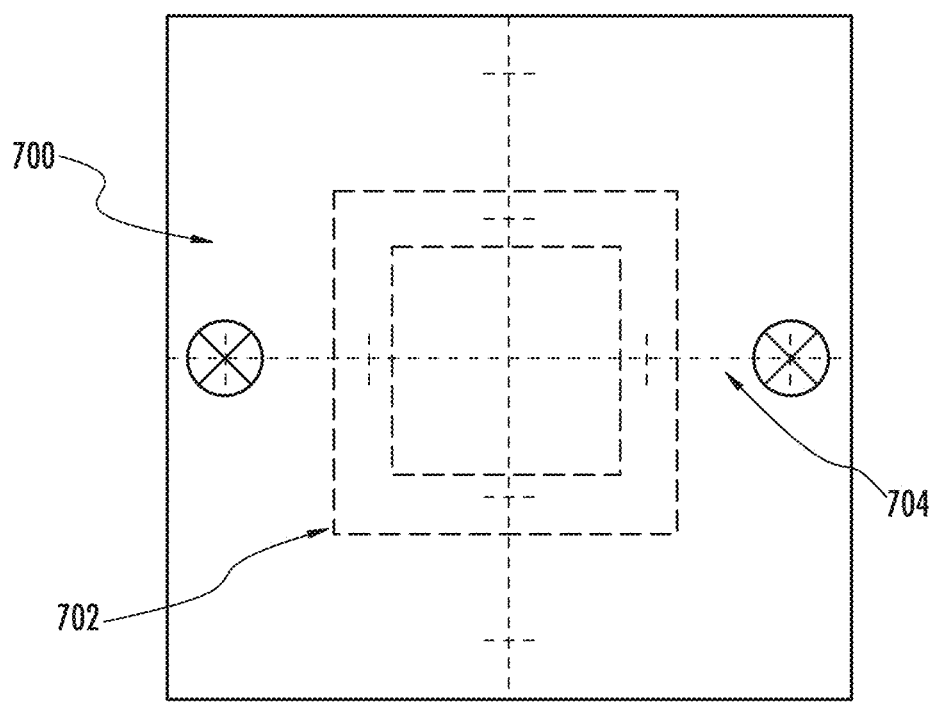

FIG. 13 illustrates an exemplary screen for defining scale in an acquired image taken using the device of the present invention.

Figure 14A:
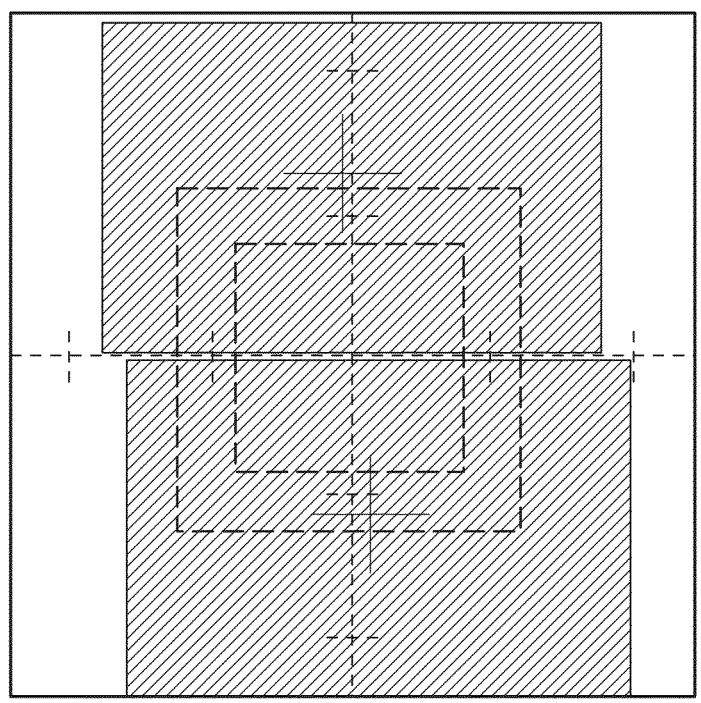

FIG. 14A illustrates an example of a program feature to superimpose images taken with the device of the present invention.

Figure 14B:
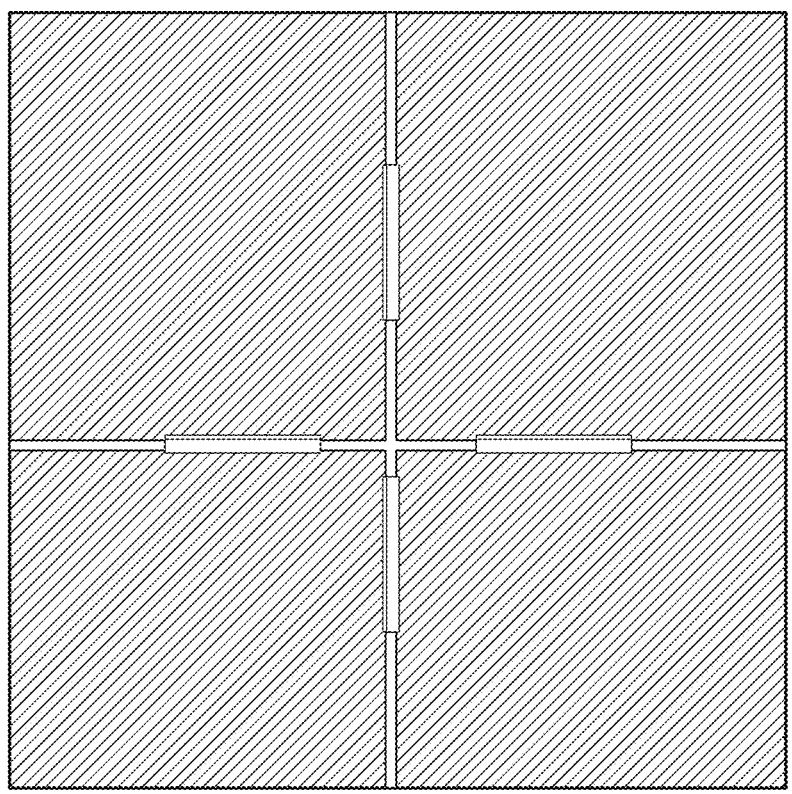

FIG. 14B illustrates an example of an image for analysis of co-linearity of the laser taken using the device of the present invention.

Figure 15:
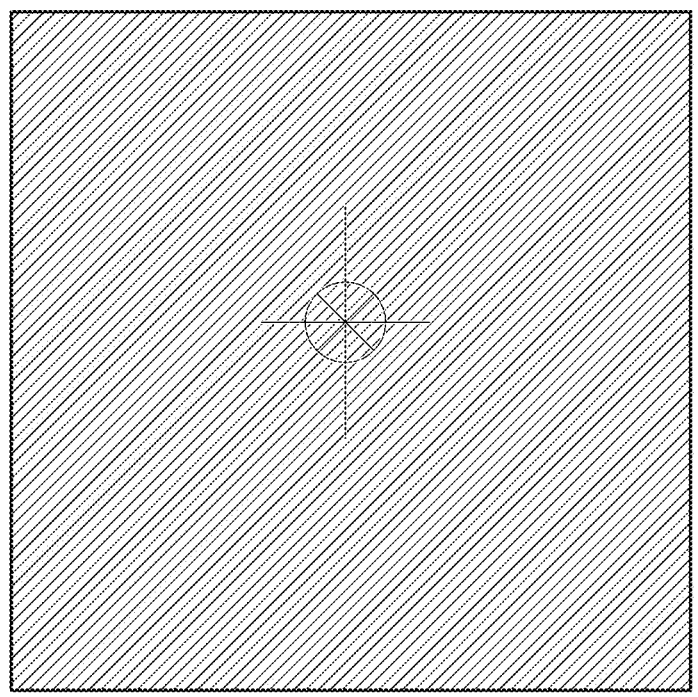

FIG. 15 illustrates an image of an exemplary recording of laser QA tasks executed with the device of the present invention.

Figure 16A:
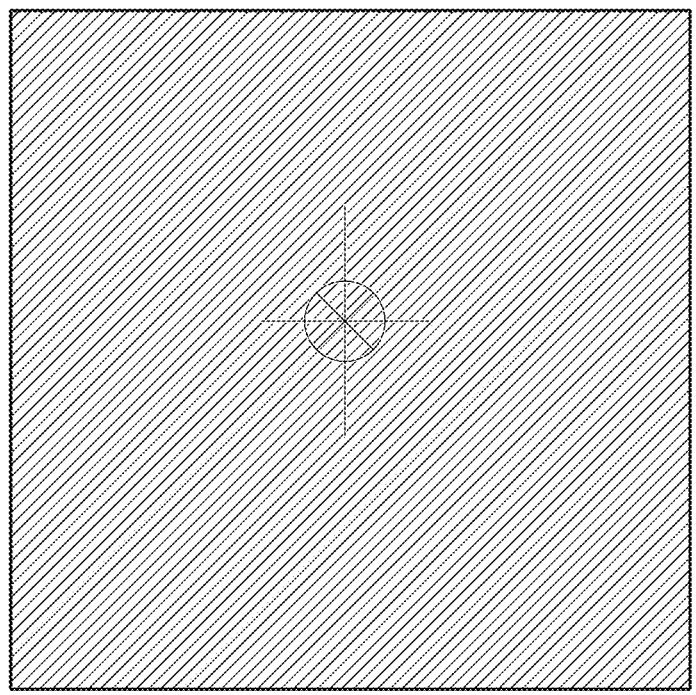
Figure 16B:
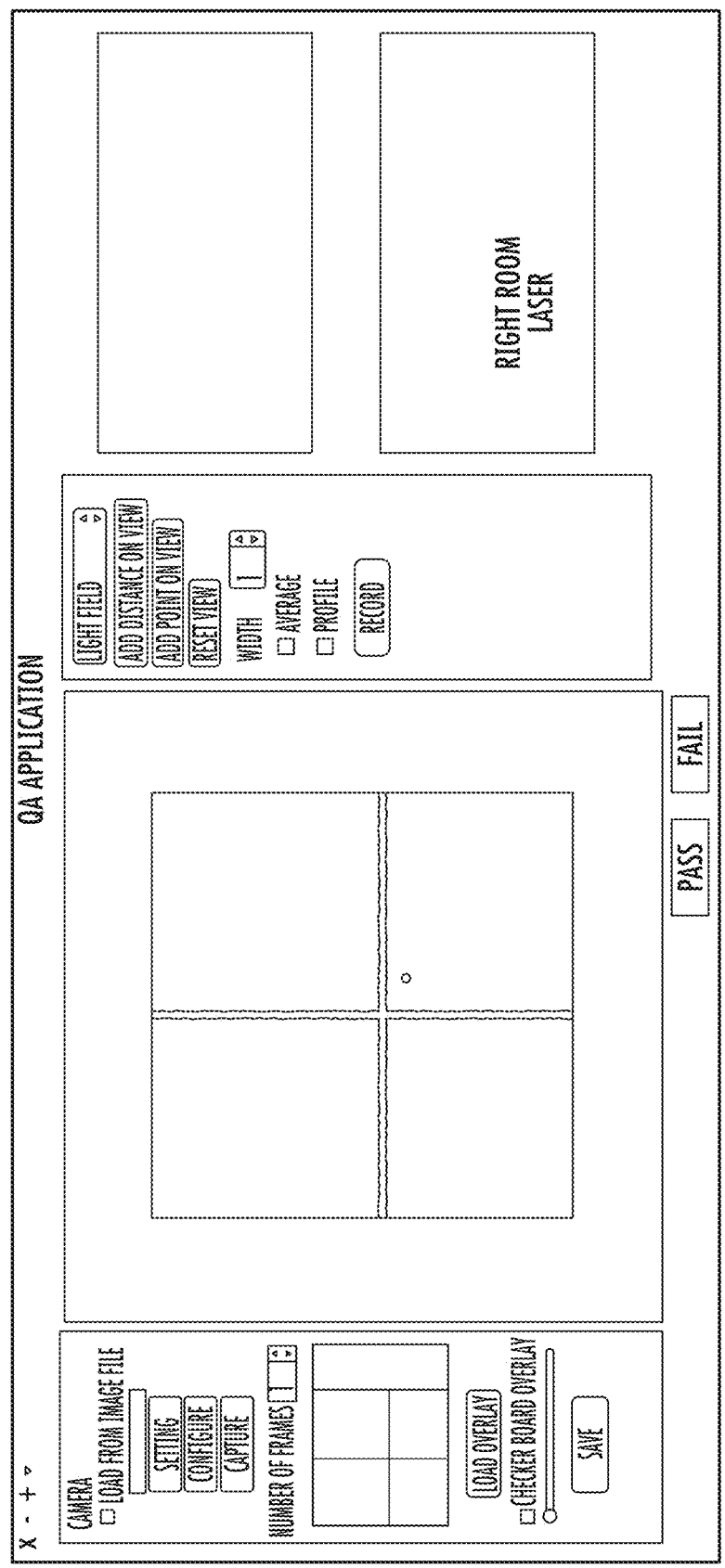

FIG. 16A illustrates an image of an exemplary recording of laser QA tasks executed with the device of the present invention. FIG. 16B illustrates an image of an exemplary embodiment of the user interface showing the acquisition of a right room laser QA.

Figure 17:
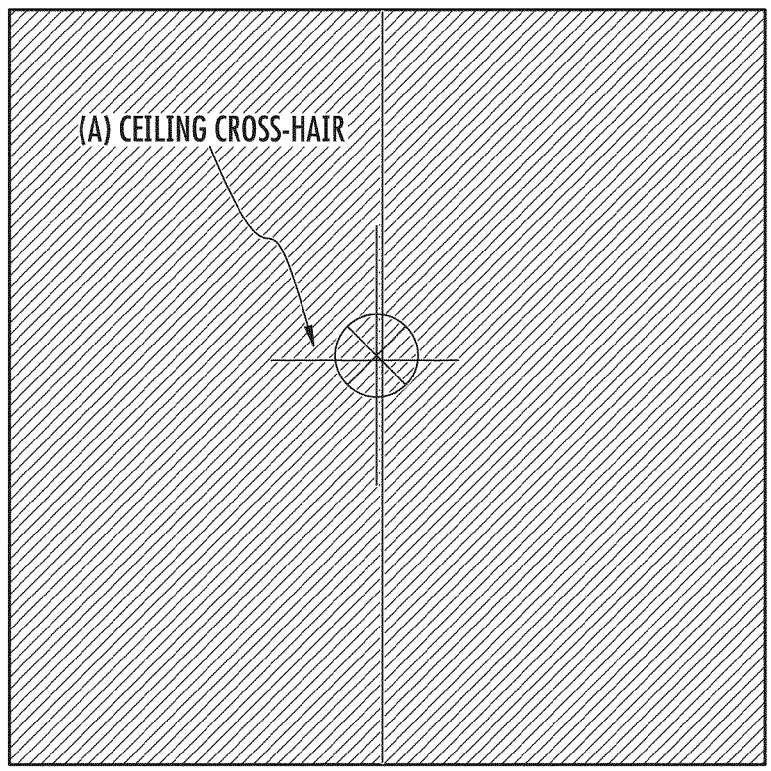

FIG. 17 illustrates an image of an exemplary recording of laser QA tasks executed with the device of the present invention.

Figure 18:
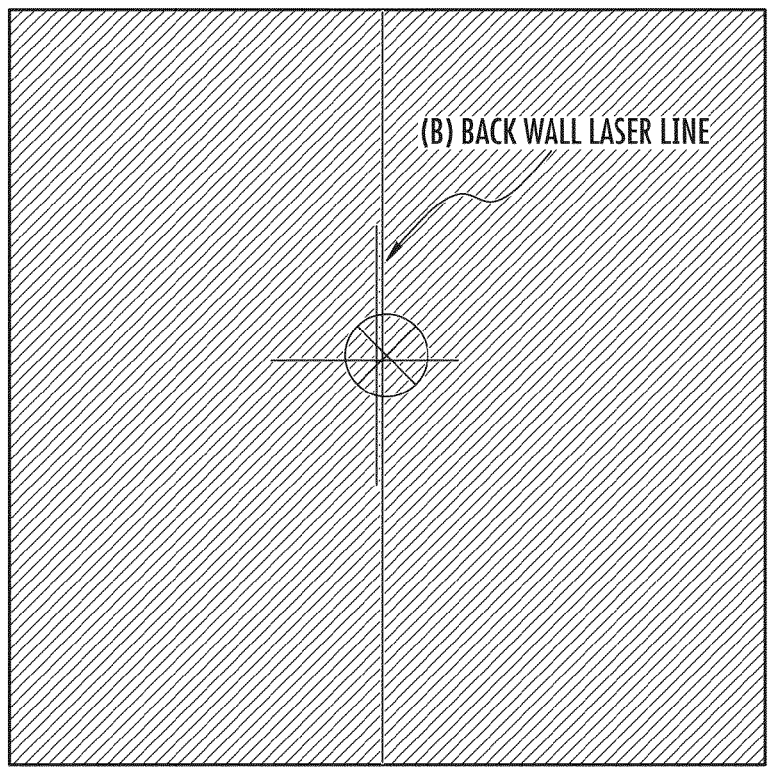

FIG. 18 illustrates an image of an exemplary recording of laser QA tasks executed with the device of the present invention.

Figure 19:
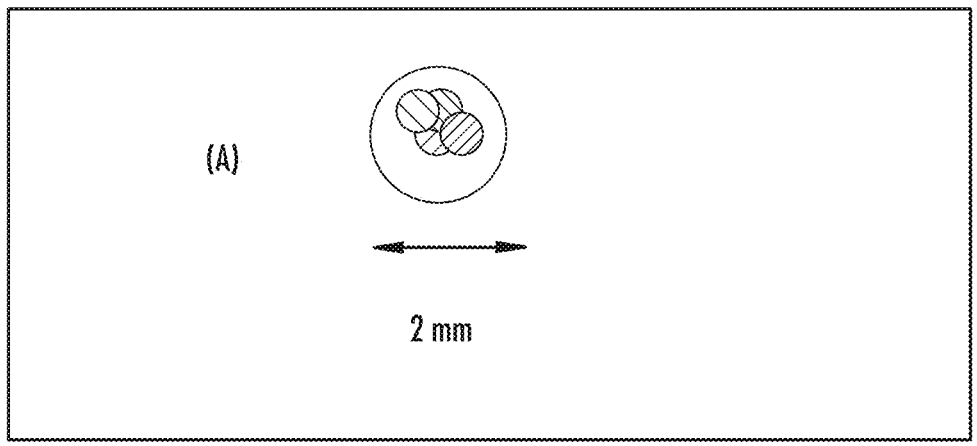

FIG. 19 illustrates laser alignment analysis using the device of the present invention.

Figure 20:
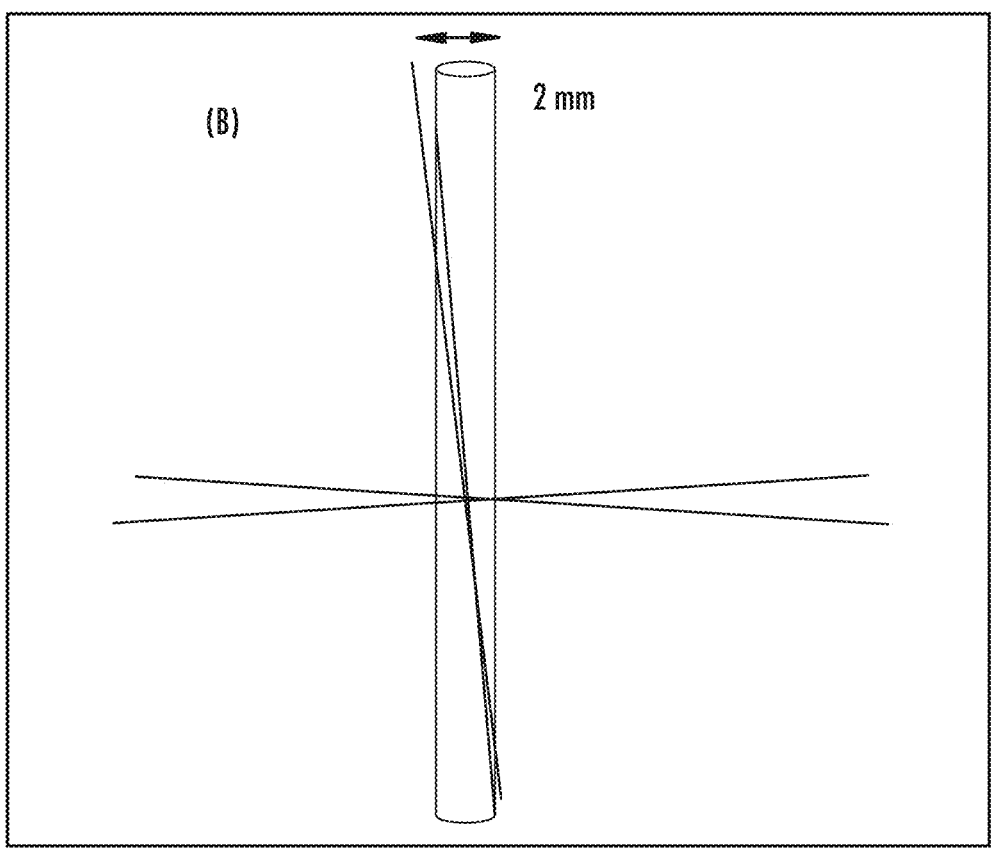

FIG. 20 illustrates laser alignment analysis using the device of the present invention.

FIGS. 21A-F, 22A-F, and 23A-C illustrate exemplary recordings of table movement and optical distance indicator (ODI) QA tasks executed with the device of the present invention. More particularly, FIGS. 21A-F relate to QA for table vertical movements captured using the device of the present invention, FIGS. 22A-F relate to QA for table lateral movements executed with the device of the present invention, and FIGS. 23A-C illustrates visual results of table rotation QA, using the device of the present invention.

FIGS. 24A-D illustrate collimator rotation QA, using the device of the present invention.

Figure 25A:
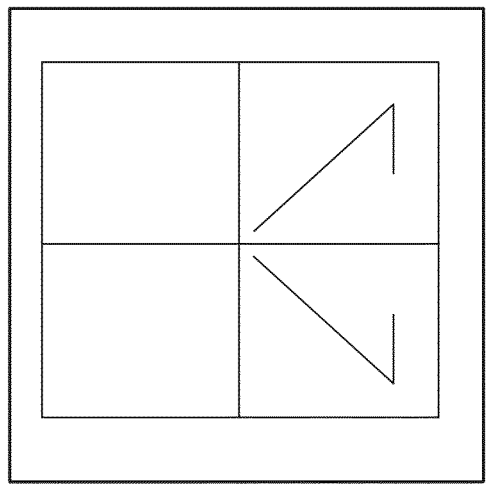
Figure 25B:
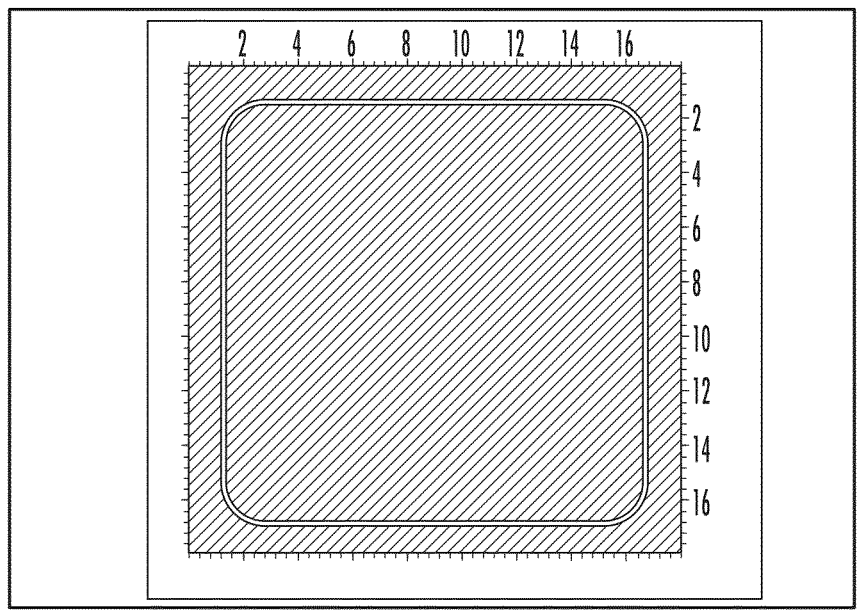
Figure 25C:
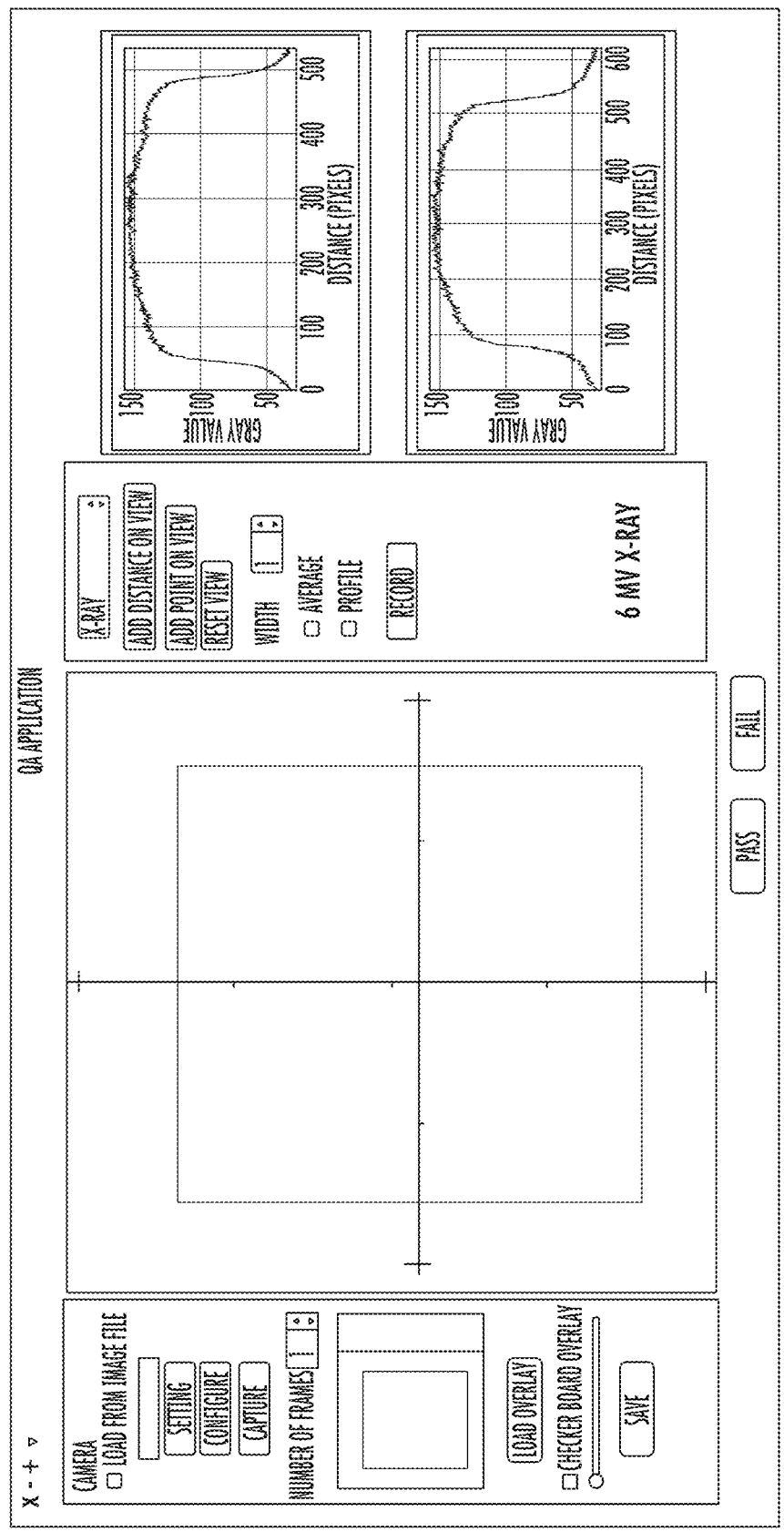
Figure 25D:
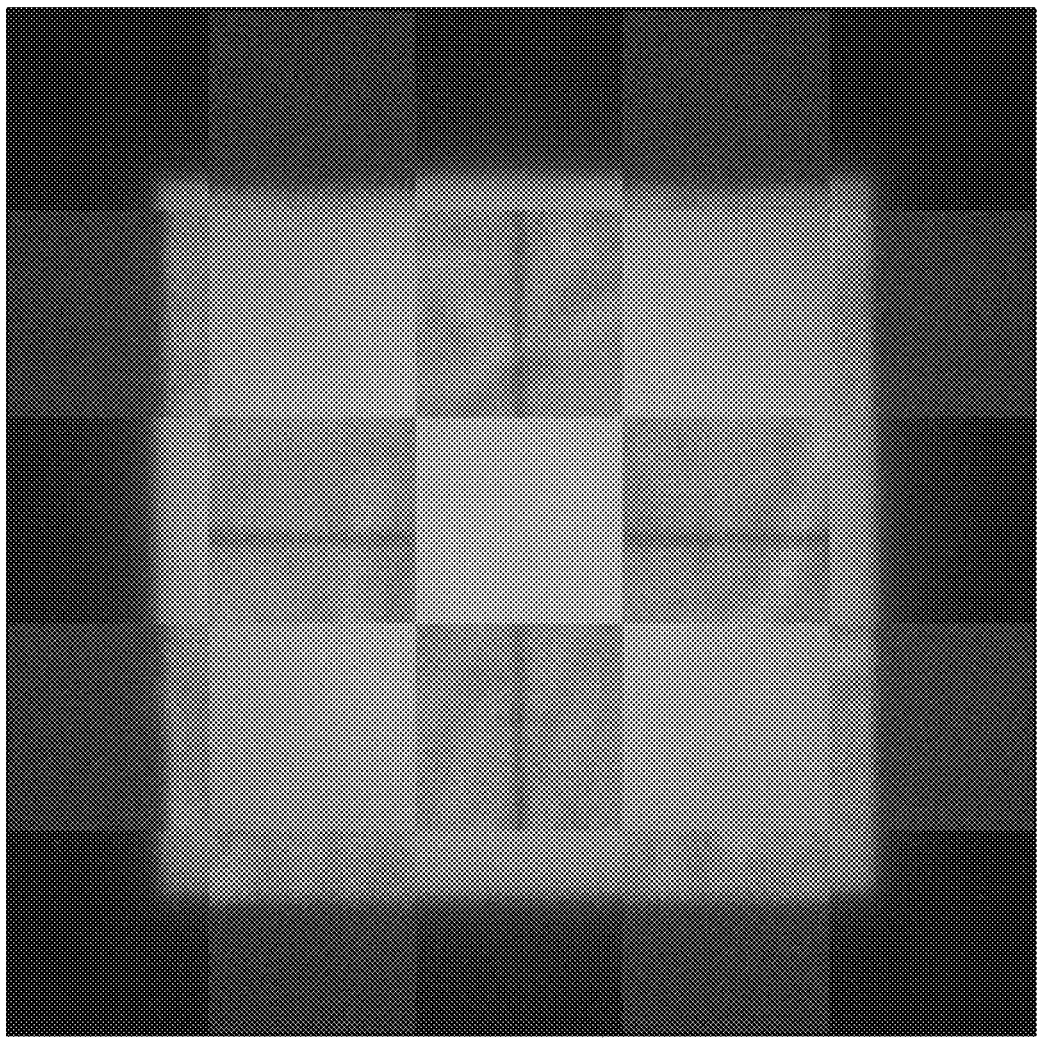

FIGS. 25A and 25B illustrate the visual results of radiation and light field congruence QA, using the device of the present invention. FIG. 25C illustrates an exemplary embodiment of the user interface showing the acquisition of a 6 MV x-ray QA, as described with respect to FIGS. 25A and 25B. FIG. 25D illustrates another example of a light field and radiation field congruence image acquired using the device of the present invention.

Figure 26:
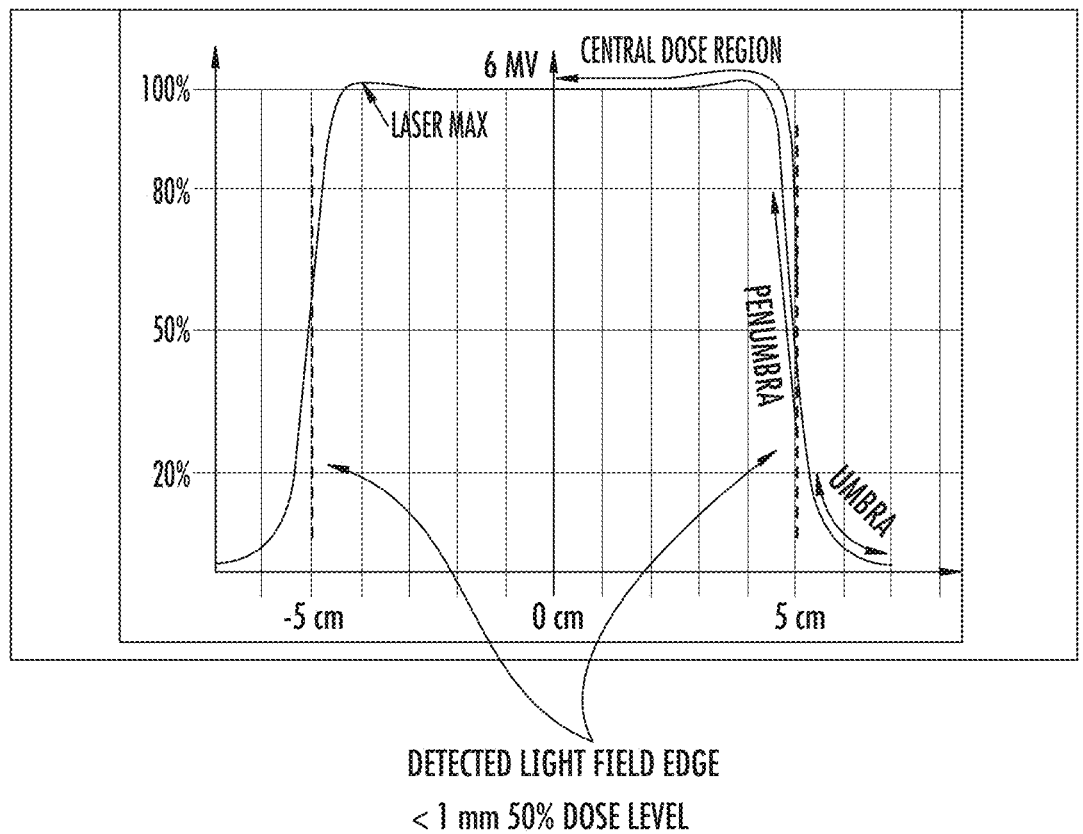

FIG. 26 illustrates a graph obtained using a profile tool in the control program for the device of the present invention.

Figure 27B:
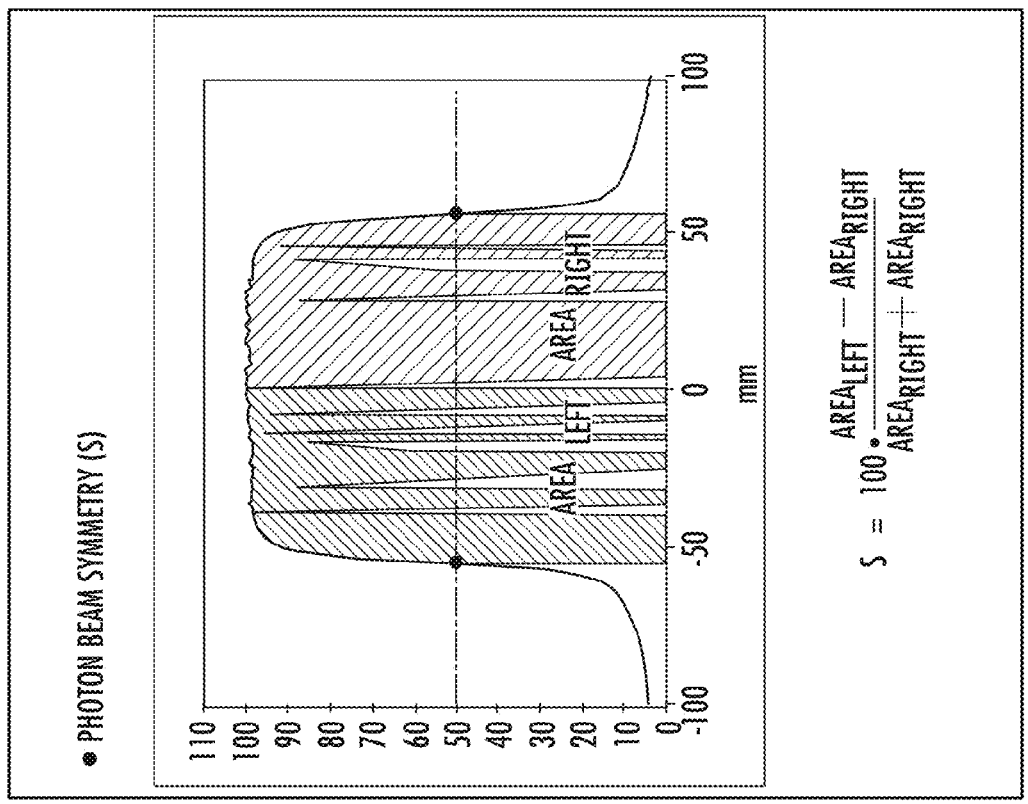
Figure 27A:
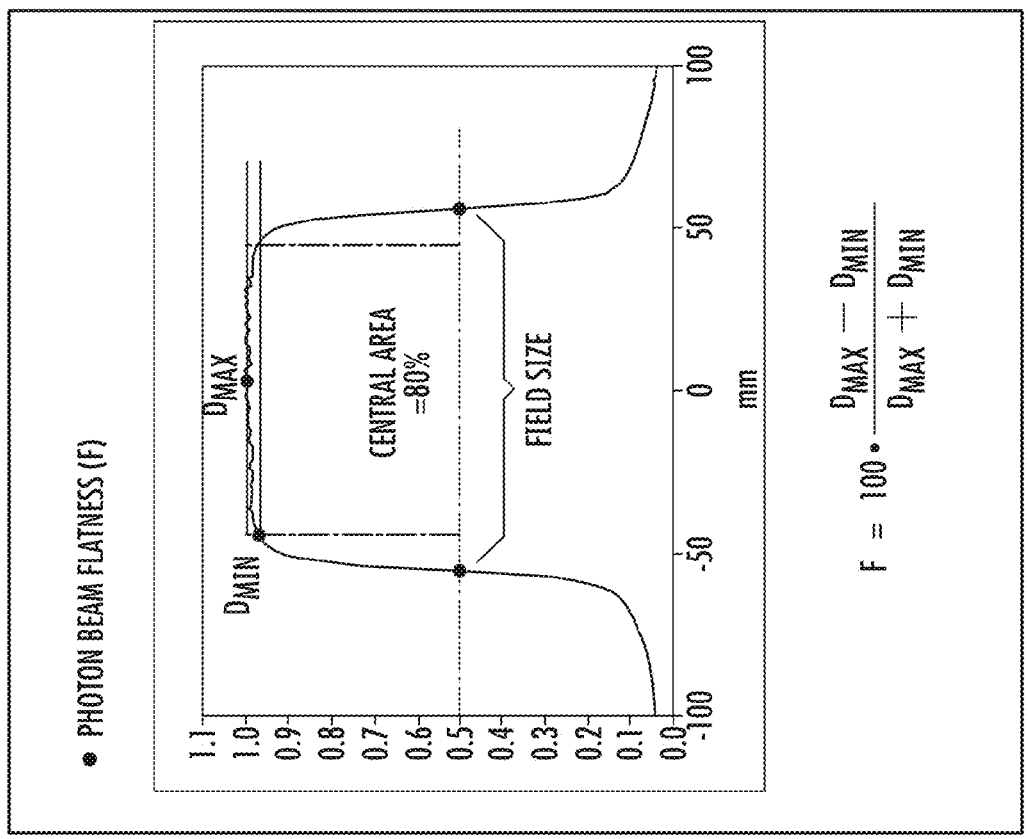
Figure 28B:
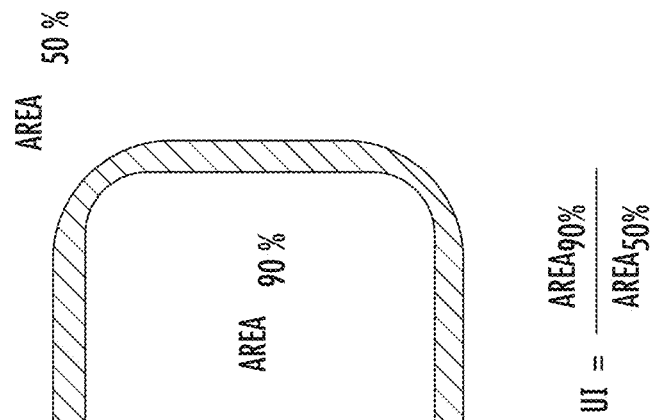
Figure 28A:
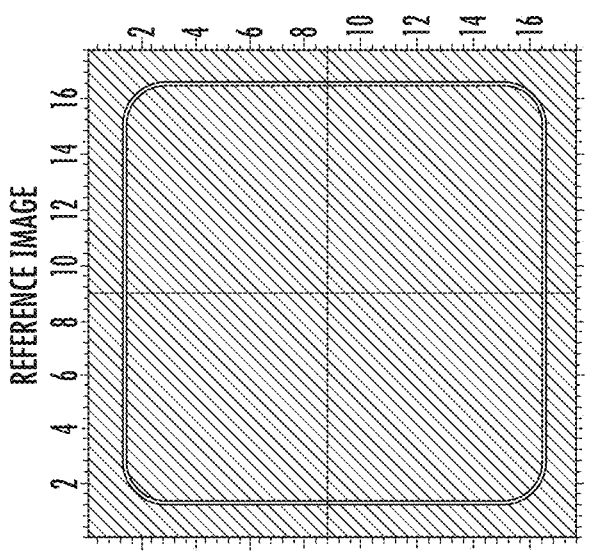
Figure 29:
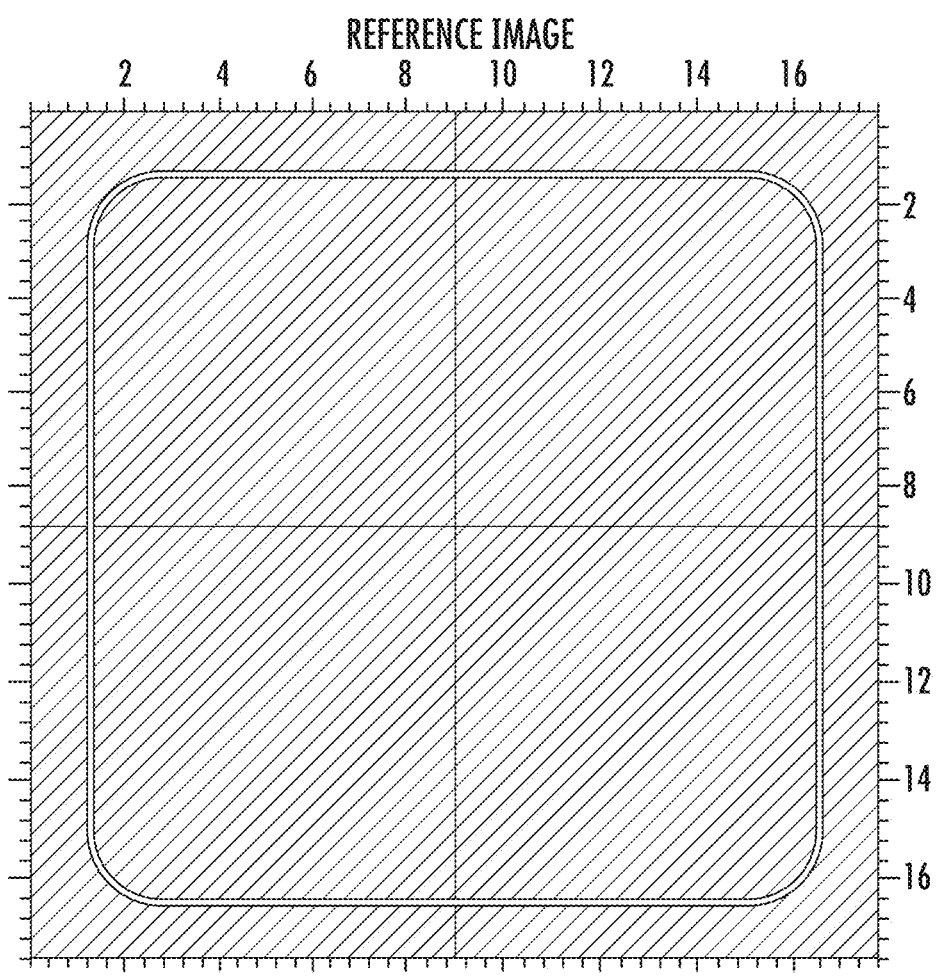
Figure 30A:
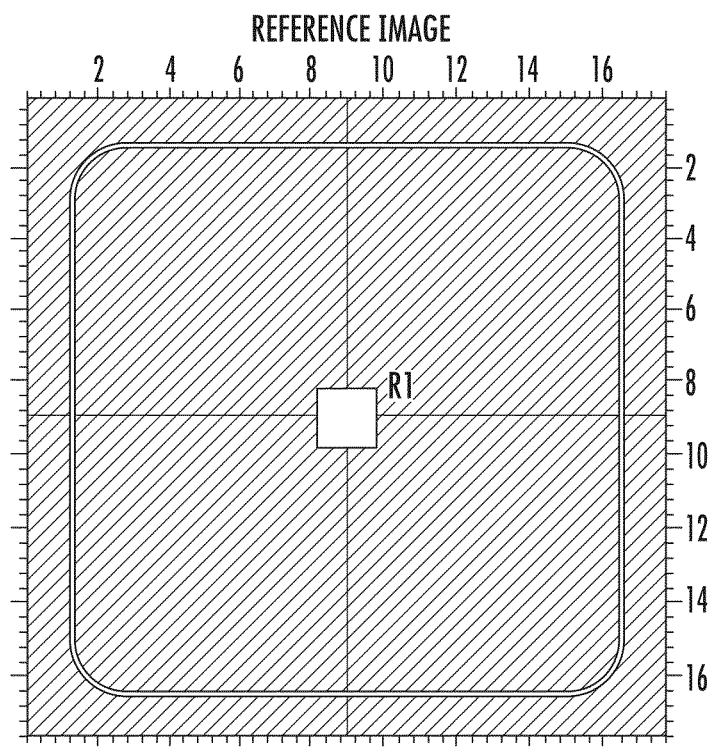
Figure 30B:
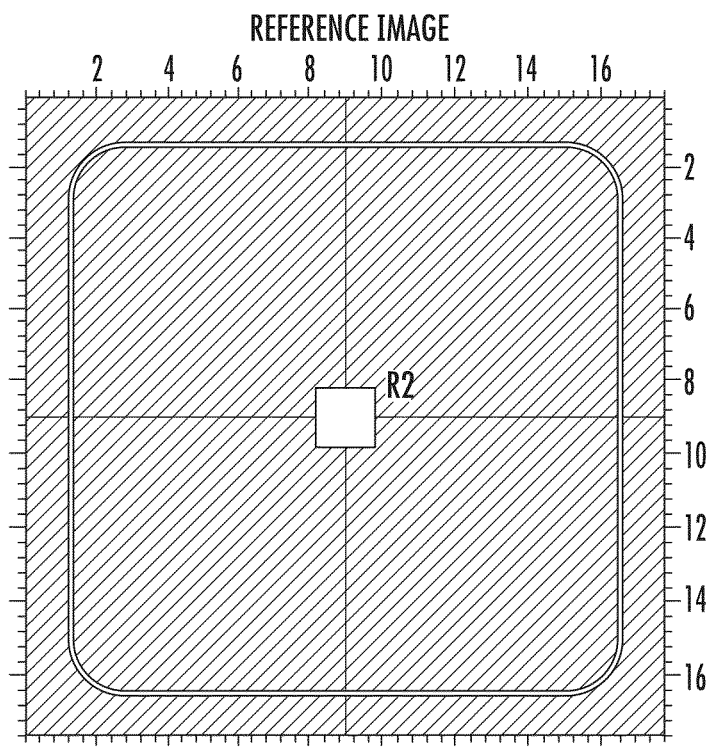
Figure 31:
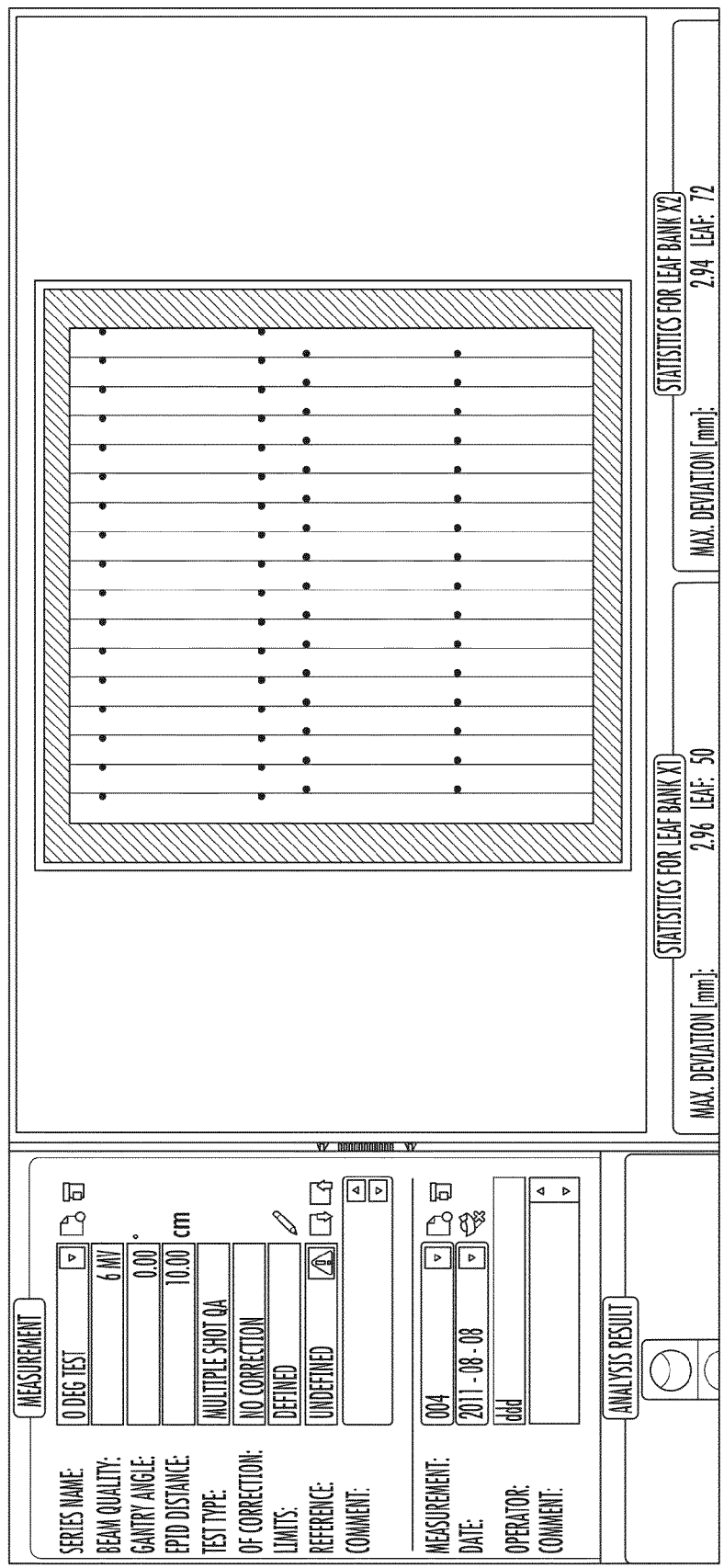
Figure 32B:
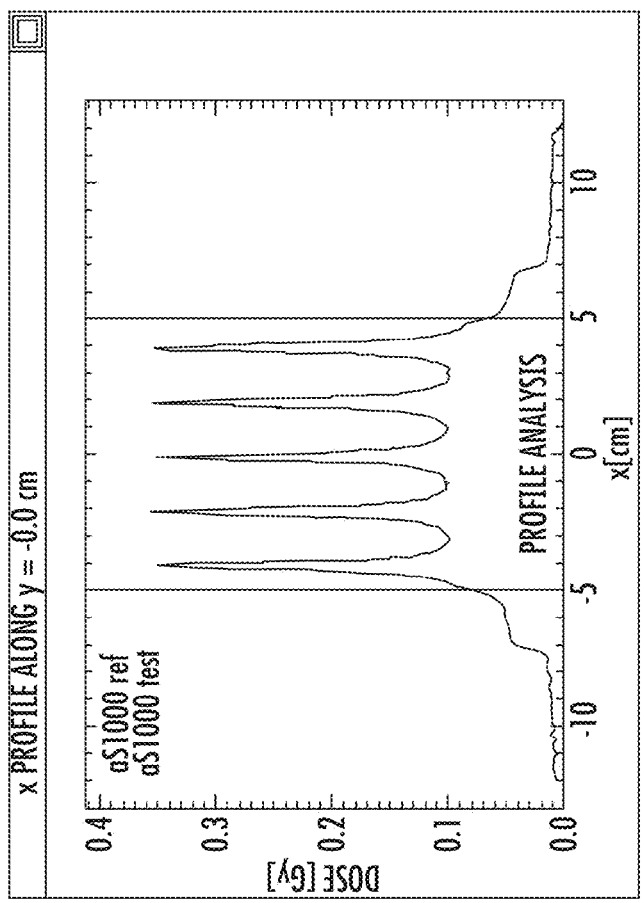
Figure 32A:
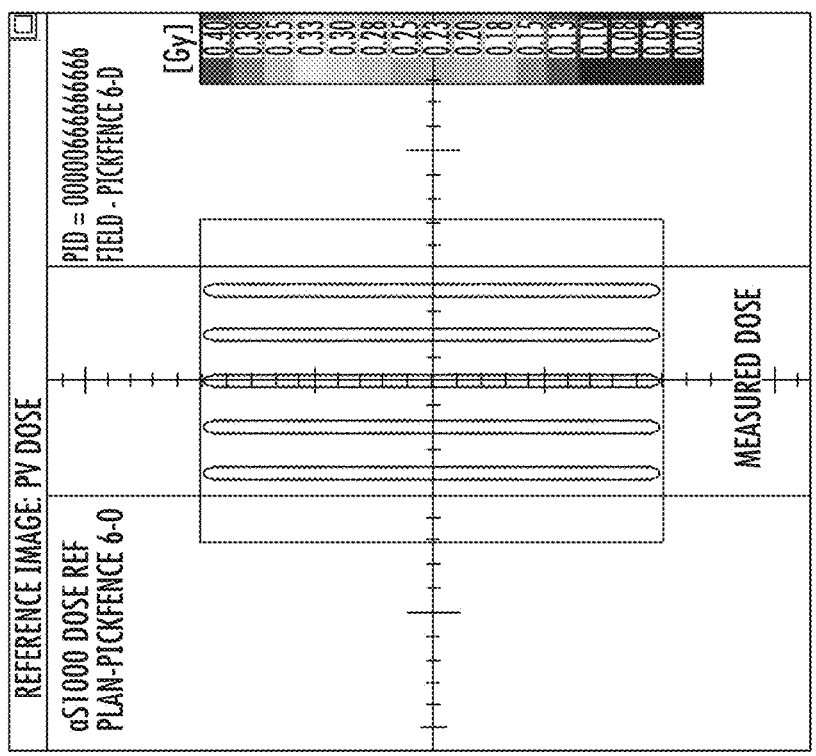

FIGS. 27A and 27B, 28A and 28B, FIG. 29 and FIGS. 30A and 30B illustrate visual representations of radiation field acquisition and analysis. More particularly, FIGS. 27A and 27B illustrate exemplary plots to show calculation methods for determining photon beam flatness and symmetry using a 1D plot, FIGS. 28A and 28B illustrate visual representations of radiation measurements taken using the device of the present invention, FIG. 29 illustrates a visual representation of a mean radiation image, taken using the device of the present invention, and FIGS. 30A and 30B illustrate exemplary visual representations of energy checks for radiation analysis.

FIGS. 31, 32A-B, and 33A-B illustrate visual representations and analysis of multi-leaf collimator (MLC) QA measurements, taken using a device of the present invention.

Figure 33B:
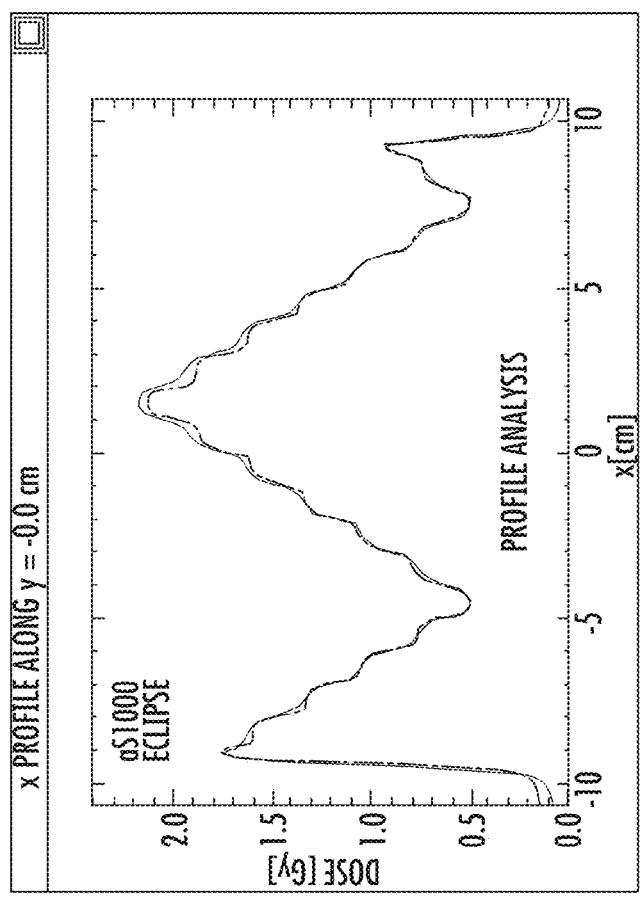
Figure 33A:
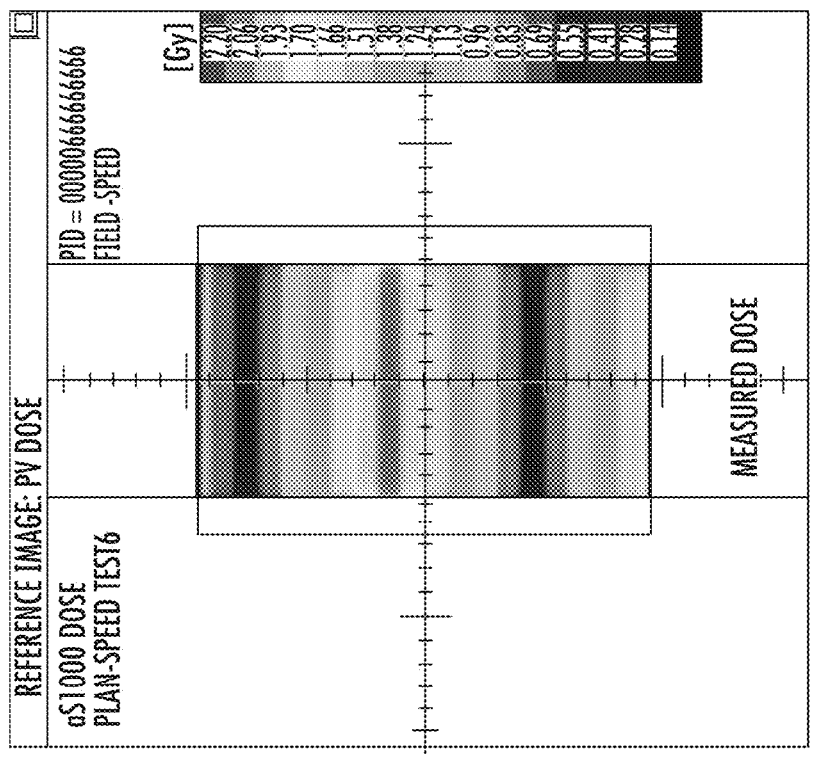

FIGS. 33A and 33B illustrate visual representations of measurement and analysis for leaf speed of the MLC.

Figure 34:
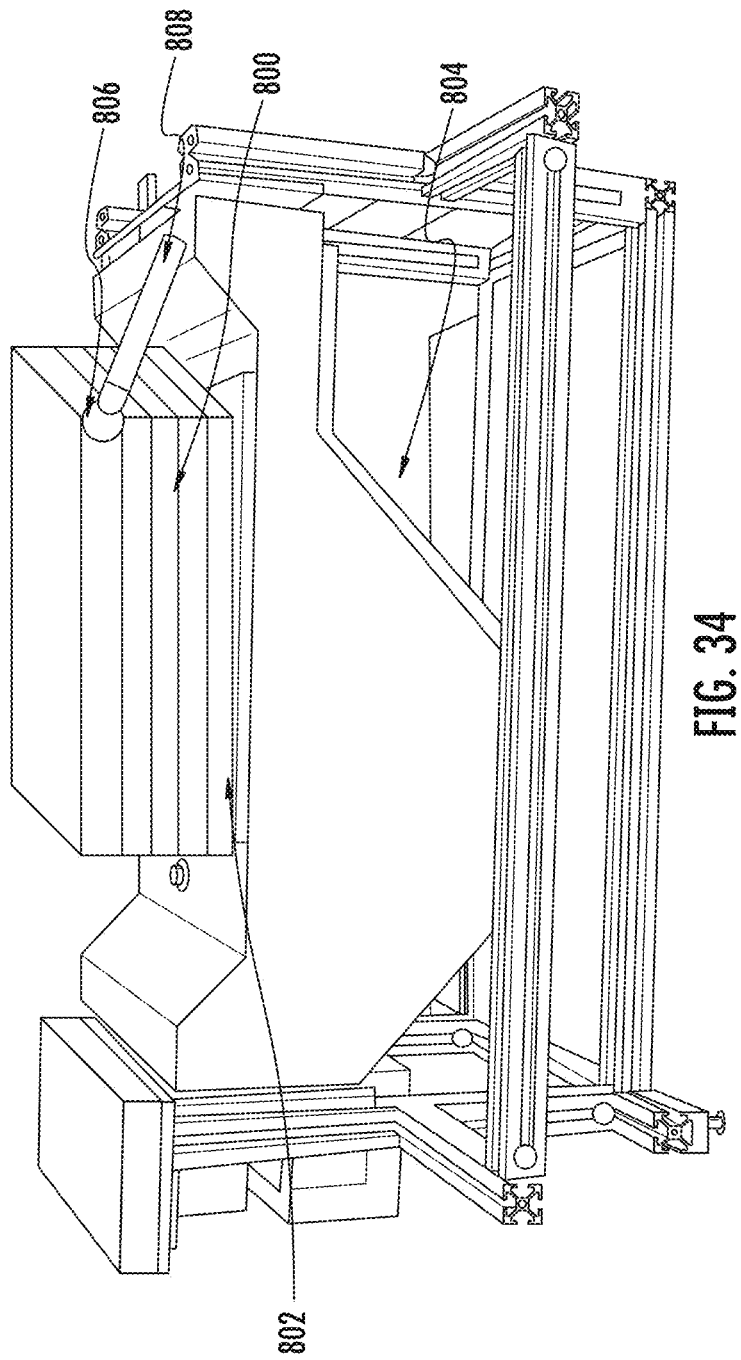

FIG. 34 illustrates a schematic diagram that the QA device of the present invention can accommodate the measurements of absolute dosimetry with an ionization chamber.

Figure 35:
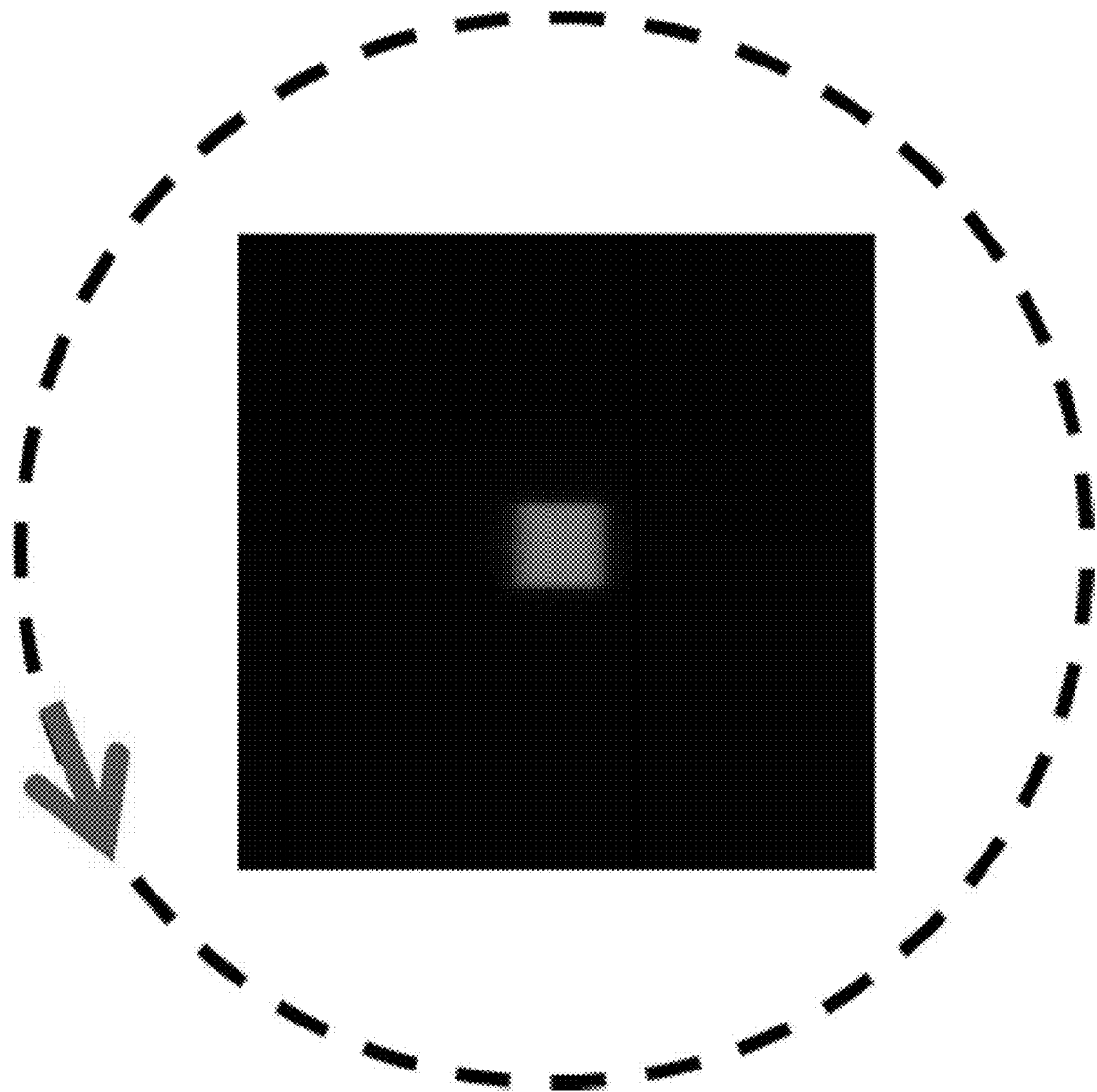

FIG. 35 illustrates an exemplary exposure of the QA device at an angle of collimator rotation in order to assess integrity of collimator rotation.

Figure 36A:
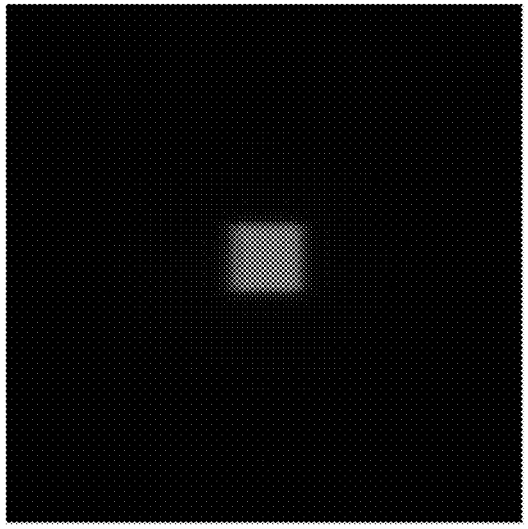

FIG. 36A illustrates an exemplary exposure of the QA device at a 0° angle of gantry rotation in order to assess integrity of gantry rotation.

Figure 36B:
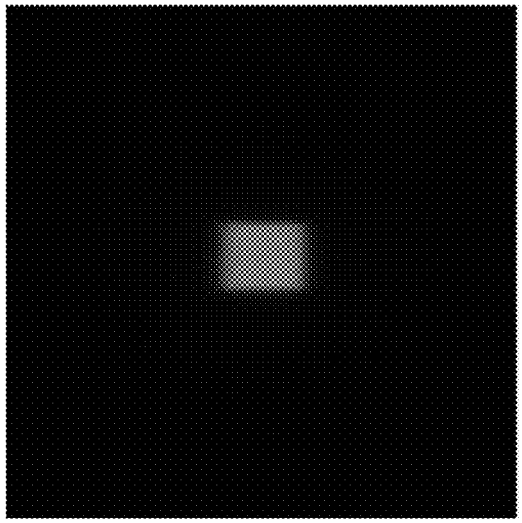

FIG. 36B illustrates an exemplary exposure of the QA device at a 30° angle of gantry rotation in order to assess integrity of gantry rotation.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention pertains to a method and apparatus for real-time mechanical and dosimetric quality assurance measurements in radiation therapy. According to an exemplary embodiment as shown in FIGS. 3A-3D, a single unifying device can be employed to perform all mechanical and dosimetric QA tasks, thereby greatly simplifying and unifying all QA tasks. The use of a digital camera ensures that all measurements can be documented for repeat analysis. As such, data can be captured in real-time in one session. In addition, the system can be integrated with the operation of the radiation machines to automate the entire process. The data can be analyzed in real-time or off-line to provide alerts about or to trend the performance of the machine in relationship with the treatment room. Accordingly, the method and apparatus of the present invention unifies measurement of mechanical motion and radiation component of the machine.

Figure 2:
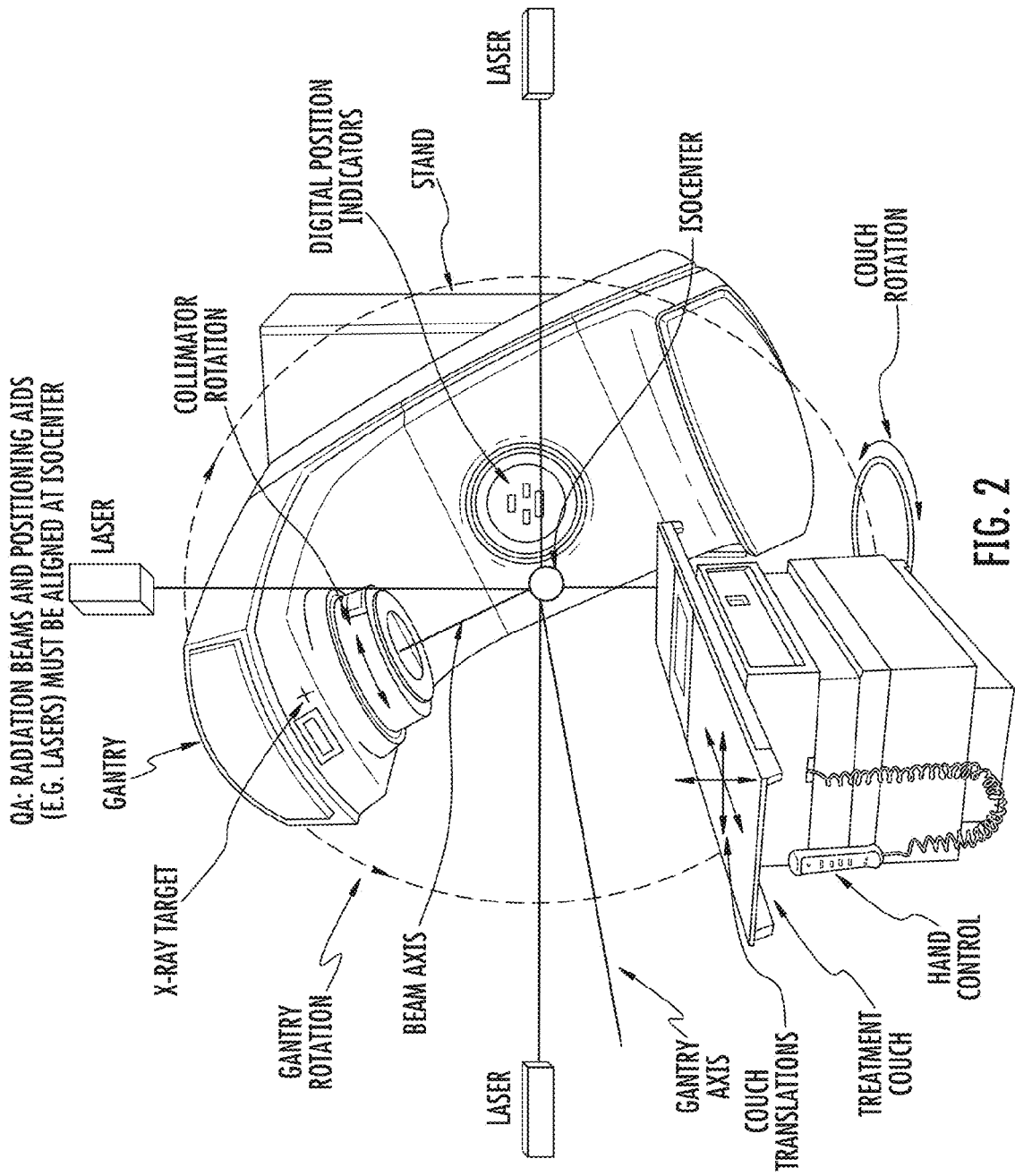
FIG. 2 illustrates a front view of a medical accelerator used for radiation treatment.
Figure 3A:
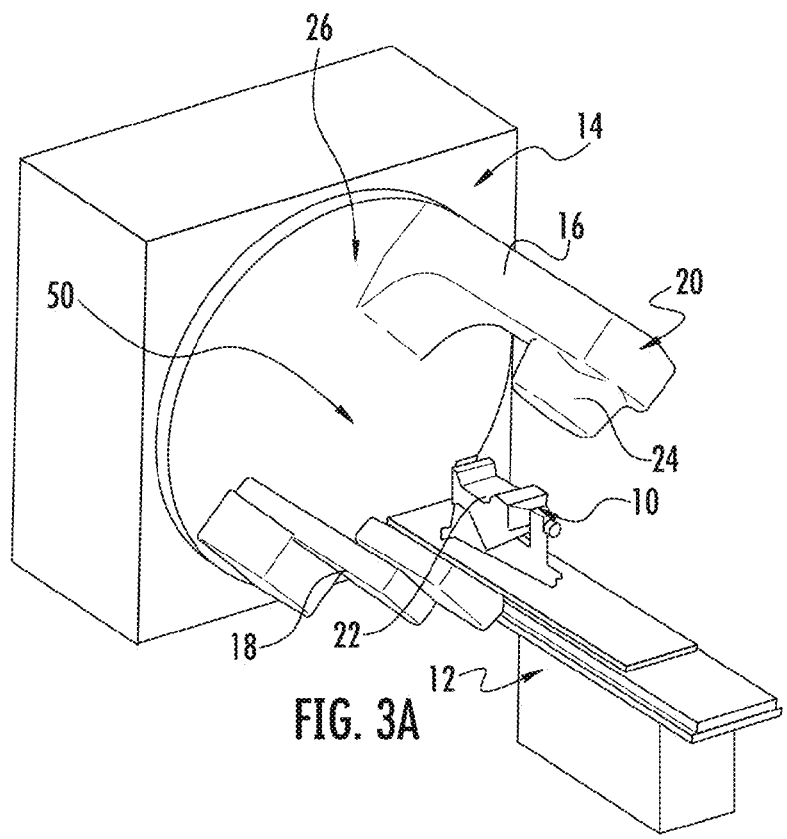
FIG. 3A illustrates a perspective view of a device according to the features of the present invention sitting within the treatment range of a medical accelerator.
Figure 3B:
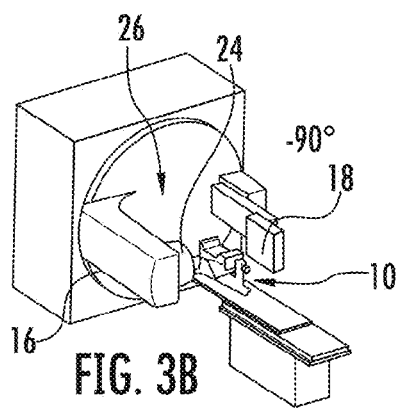
FIG. 3B illustrates a perspective view of a device according to the features of the present invention sitting within the treatment range of a medical accelerator.
Figure 3C:
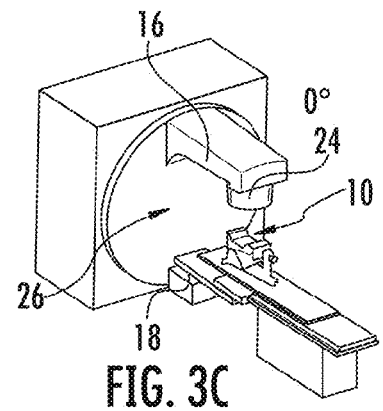
FIG. 3C illustrates a perspective view of a device according to the features of the present invention sitting within the treatment range of a medical accelerator. FIG.
Figure 3D:
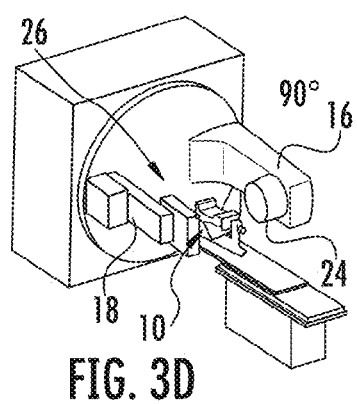

FIGS. 3A-3D show the operation principles of the system. In FIGS. 3A-3D, the device 10 is placed on the patient couch 12 of the radiation treatment room. The device 10 is positioned adjacent to a medical accelerator 14 to undergo QA measurements, such that the device 10 is positioned between jaws 16, 18 of the medical accelerator 14 including a multileaf collimeter (MLC) 24 and a gantry 26. When placed on the couch 12, the device 10 can be rotated continuously from approximately +90° to −90°, so as to view the radiation or optical images of the gantry 26 as it rotates from approximately +90° to −90°. The device can also be rotated a full 360°, when it is supported to suspend off the edge of the couch. FIG. 3A illustrates the jaws 16, 18, the gantry 26, and the MLC 24 in an intermediate position between approximately 0° and 90°. FIG. 3B illustrates the jaws 16, 18, the gantry 26, and the MLC 24 in a position at approximately −90°. FIG. 3C illustrates the jaws 16, 18, the gantry 26, and the MLC 24 in a position at approximately 0°, and FIG. 3D illustrates the jaws 16, 18, the gantry 26, and the MLC 24 in a position at approximately 90°.

Also, as illustrated in FIGS. 3A-3D, for radiation QA measurements, including complex intensity modulated treatment, an imaging surface 22 for receiving multiple energy sources will be used. The imaging surface 22 can take any form known to one of skill in the art for receiving the multiple energy sources. More particularly, a phosphor screen or a scintillator sheet can be used to capture the multiple energy sources. The phosphor screen is also used for optical imaging of light fields, optical indicator, and laser paths. The imaging surface 22 can also include markings to show spatial calibration. By placing the device in a position not obstructed by the treatment head 20, the system can be used to capture optically the positions of all lasers and other alignment indicators in the room, as well as the integrity of mechanical motions of the medical accelerator 14 including jaws 16, 18, MLC 24, gantry 26, and couch 12. This is a major improvement since these optical measurements are currently visually noted and recorded as texts in the QA document. The use of a common phosphor screen or scintillator sheet for both radiation and optical imaging is also an important, yet to be reported in the ART, discovery, because it renders un-necessary the replacement of the phosphor screen for optical imaging.

FIGS. 4A-4C illustrate views of the device 10 in further detail according to the features of the present invention. FIG. 4A illustrates a perspective view of a first side of the device 10, while FIG. 4B illustrates a perspective view of a second side of the device 10, both according to the features of the present invention. FIG. 4C illustrates a perspective view of the device rotated to a position of about −45°. As illustrated in FIGS. 4A-4C, the device 10 includes a housing 21 and a camera 28. The camera can take the form of a conventional digital camera or a radiation resistant camera. It should be noted that if a conventional digital camera is used a shield, described further herein, can be used to protect the camera from radiation and to lower the overall cost of the device from a model including a radiation resistant camera. The camera 28 is further configured to measure and record data related to multiple energy sources used in radiation therapy. The camera 28 also includes a lens 29. In order to divert data from the multiple energy sources to the camera 28, at all medical accelerator 14 gantry 26 angles, the device 10 also includes a mirror system 30. The mirror system 30 includes an internal three-mirror arrangement that will be described in further detail with respect to FIGS. 5A-5D. While a three-mirror arrangement is shown here as an exemplary embodiment, any functional mirror system could be used as long as it maintains a stationary camera position while the receptor phosphor screen rotates about the isocenter plane of the accelerator 14 gantry 26.

Further, as illustrated in FIGS. 4A-4C, the device 10 is mounted on a rotary table 34. The rotary table 34 allows for the device 10 to be rotated between approximately −90° and 90° such that the imaging surface 22 and the mirror system 30 can remain aligned with the gantry 26 to record data. The rotary table 34 can also include a base support 36. The base support 36 includes leveling feet 38 and a bubble level 40. The leveling feet 38 and the bubble level 40 allow for the device 10 to be leveled for optimal operation, when placed for a QA analysis of a medical accelerator. The rotary table 34 can also include arms 42, 44, which hold and suspend the device 10, slightly above a top surface 46 of the base support 36. This allows the device 10 to rotate freely about an axis "A" of the rotary table 34. The mechanism for rotation can take the form of any suitable mechanism for rotating the device 10 from approximately −90° to 90°. In another embodiment, the entire base can be designed to rotate with the arms 42, 44 and device 10, such that the measurements can be acquired in full 360° rotation.

FIGS. 5A-5D shows the internal three-mirror arrangement 30 which can be rotated to capture data from different gantry angles. This three-mirror arrangement 30 within housing 21 allows the placement of the image plane 48, i.e., the imaging surface 22, at the plane of the machine isocenter 50 which is the calibration center of all machine parameters. Most importantly, the camera 28 is stationary and positioned to be on the same axis as the imaging plane. As such, the image plane 48 is co-linear with an axis "B" through the longitudinal center of the camera 28. Additionally, the image plane 48 can be rotatable about the axis "B" of the camera 28. It should also be noted that the camera 28 can be kept stationary while the device 10 rotates about the camera 28.

Further, as illustrated in FIGS. 5A-5D, a first mirror 52 is positioned on a first lower wall 54 of the housing 21 of the device 10, across from the camera 28. A second mirror 56 is positioned on a second lower wall 58 of the housing 21 of the device 10 and adjacent to the first mirror 52 positioned on the first lower wall 54. The first mirror 52 and the second mirror 56 are separated by an angle. Any suitable angle of separation can be used so long as the data is properly transmitted to the camera 28. A third mirror 60 is positioned in a first plane parallel to a second plane in which the second mirror 56 is disposed. The first plane is separated from the second plane by a distance. The distance can be any distance suitable for transmitting the data to the camera 28. Preferably, all mirrors are set at 45 degree to allow 90 degree reflection. This is not a necessary requirement, as robotics can be used to provide 90 degree reflection, or software can be used to correct imperfect reflection.

Generally, data from the treatment head 20 is transmitted along a trajectory path 68. Trajectory path 68 travels perpendicularly through the imaging surface 22 and reflects off of the first mirror 52 at an approximately 90° angle. Preferably, the angle will be exactly 90°. Imperfect 90° will be corrected by software. The trajectory path 68 then travels across an interior space 70 defined by walls of the device 10 to be reflected off of the second mirror 56 at an approximately 90° angle. The trajectory path 68 then continues vertically to be reflected off of the third mirror 60 at an approximately 90° angle. After being reflected off of the third mirror 60, the trajectory path 68 continues on through the lens of the camera 28 for recording of the data travelling along the path 68. While a specific mirror system is described above, this example is not meant to be limiting. Indeed, the mirror system can be configured such that it has one or more stationary or adjustable-position mirrors or a combination thereof. Additionally, the mirror system can be rotatable in order to capture data from different gantry angles.

Also, as illustrated in FIGS. 5A-5D, as the device rotates, the third-mirror directs all data from the image plane to the camera. The camera can be held stationary to capture any rotated views that can be digitally corrected or the camera can be rotated in its stationary position with the mirror subsystem so that no image correction is needed. The stationary camera offers advantage in the simplicity of set up. A computer can also be included in the system for collecting and analyzing the data. The computer includes a feedback loop for automatic control of the device 10. More particularly, the device 10 can be programmed to move in synchrony with mechanical components of the medical accelerator about the isocenter. Measurements are made in real time. The system can be extended for QA of the kilovoltage imaging system, as well as the positioning of radioactive sources in brachytherapy. Software tools can be implemented to analyze, evaluate and trend the performance of the treatment unit and the integrity of in-room alignment accessories.

FIG. 6 illustrates a partially sectional view of a QA device according to an embodiment of the present invention. As described above with respect to FIGS. 5A-5D, FIG. 6 illustrates a partially sectional view of the device 100. An embodiment of the internal mirror arrangement 130 is illustrated, within housing 121. The internal mirror arrangement 130 allows the placement of the image plane 148, i.e., the imaging surface 122, at the plane of the machine isocenter.

Further, as illustrated in FIG. 6, a first mirror 152 is positioned on a first lower wall 154 of the housing 121 of the device 100. A second mirror 156 is positioned on a second lower wall 158 of the housing 121 of the device 100 and adjacent to the first mirror 152 positioned on the first lower wall 154. The first mirror 152 and the second mirror 156 are separated by an angle. Any suitable angle of separation can be used so long as the data is properly transmitted to the camera. A third mirror 160 is positioned in a first plane parallel to a second plane in which the second mirror 156 is disposed. The first plane is separated from the second plane by a distance. The distance can be any distance suitable for transmitting the data to the camera. The device can also include a fourth mirror 172 positioned, such that it shields the camera from direct radiation from the medical accelerator. The fourth mirror 172 is also positioned at an angle such that the data is transmitted from the third mirror 160 to the camera.

FIG. 7 illustrates a diagram of a method in accordance with the features of the invention. The method 200 is directed generally to real-time mechanical and dosimetric quality assurance measurements in radiation therapy. The method 200 includes a step 202 of providing an imaging surface for receiving multiple energy sources. More particularly, the imaging surface has an imaging plane positioned on a same plane as an isocenter of a medical accelerator. Step 204 includes directing the multiple energy sources to a camera. Additionally, step 206 can include measuring and recording the data related to the multiple energy sources.

FIGS. 8A and 8B further illustrate methods of assessment of two of the many QA criteria to be performed on a medical accelerator, in accordance with the features of the invention. As shown in FIGS. 8A and 8B, multiple energy sources can be directed at the device 300, and can thus be recorded by the device 300. In FIG. 8A, a radiation beam 308 from the medical accelerator 304 is directed at the device 300. The radiation beam 308 is directed at the device 300, such that it travels through the imaging surface 322, in this case a phosphor screen. The light 309 from the phosphor screen can then be measured by the camera 328, as shown in sample image 310. The camera 328, can then transmit the data to computer 312 for recording and analysis, either through a wired or wireless connection. In FIG. 8B, room lasers 314, 316 at isocenter plane can be directed at an imaging surface 322 of the device 300. The phosphor screen can also be used as the image receptor 318 at the imaging plane 322 with an overlaying scale 320 or a digitally encoded scale. The projection of the room lasers 314, 316 is measured by the camera 328, and the data can then be transmitted to a computer (not pictured) for recording and analysis.

FIG. 8C illustrates a method of performing table positioning QA, according to an embodiment of the present invention. Previously, table positioning QA was measured visually. Optical Distance Indicator (ODI) verification is used, which is a verification of a lateral laser. The laser, which mimics the source of radiation, is shined onto the device of the present invention, which is disposed on the patient table and rotated 90° to view the lateral room laser. The correctness of the positioning of the laser was previously assessed visually, and no recording of the positioning could be made. Using the device of the present invention, the ODI can be recorded and assessed. The recording can also be saved for any later review, or verification of the proper function of the medical accelerator. As illustrated in FIG. 8C, the ODI is recorded at 90 cm, isocenter (or 100 cm), and 110 cm. FIG. 8C also illustrated the table in an up or lifted position, at isocenter, and in a down or lowered position.

FIG. 8D illustrates a method of performing rotation or optical QA, according to an embodiment of the present invention. This method measures the accuracy of the rotation of the collimator, and before the device of the present invention, this QA measurement was not recorded. To check collimator rotation, a technician directs a light source that mimics the radiation beam onto the device of the present invention, which is disposed on the patient couch. The technician rotates the collimator to observe that the light moves correctly about the isocenter of the medical accelerator. As illustrated in FIG. 8D, the rotation of the collimator is measured about the isocenter (100 cm). Rotation of the collimator is measured at rotations of 90, 180, 270, and 360 degrees. Using the device of the present invention, the position of the light source can be recorded, as illustrated in FIG. 8D.

FIG. 8E illustrates a method of performing optical and radiation coincidence of a field shaped by the multi-leaf collimator. As illustrated in FIG. 8E, the device of the present invention can be used to record not only a light field shaped by the multi-leaf collimator, but also a radiation field shaped by the multi-leaf collimator. Further as illustrated in FIG. 8E the coincidence of the light field and the radiation field can be superimposed with the radiation image in order to ensure accuracy of the radiation field. The recorded images can be kept to show proper function of the medical accelerator. Additionally, like the methods of measurement of QA discussed with respect to FIGS. 8C and 8D, the method of performing optical and radiation coincidence has not previously been recorded.

Additionally, software can be incorporated into a system of operating the present invention. Incorporating software would allow the present invention to be further automated, saving even more time for a medical physicist performing QA on a medical accelerator. The device of the present invention can include a microprocessor, computing device, or other means of providing computer control to the device known to or conceivable by one of skill in the art. Alternately, the software can be loaded onto a separate computing device, server, or remote server and can communicate wirelessly or with a wired connector to a control device housed in the device of the present invention. Such a set-up would allow for multiple QA devices to be controlled by one separate computing device, server, or remote server. Any other software control set-up known to or conceivable by one of skill in the art could also be used. The device can also include robotic control to translate movement commands from the computer program into movement of the device. Additionally, the operation of the device can be integrated with the operation of the medical accelerator For instance, as far as mechanical features, the software can be used to control or measure at least the colinearity and convergence of the lasers, table movement and optical distance indicator, as well as collimator movement. With respect to radiation features, the software can be used to control or measure at least light and radiation field congruence, radiation profile constancy, and energy constancy. The light and radiation field congruence can be controlled at least with respect to the x-ray beams, flatness and symmetry, and conformity index. The radiation profile constancy can be controlled at least with respect to electron beams, and the energy constancy can be controlled at least with respect to x-ray and electron beams.

Another software tool can be configured for setting the camera. In performing a QA analysis, the technician can use the software to set the camera, including but not limited to setting the time of integration and a number of frames to be acquired. The settings can be stored as a file in order to streamline QA testing further. For instance, settings for optical related QA testing can be stored as a file, while settings for radiation related QA testing can be stored as a separate file. When the technician is ready to engage in either QA testing protocol, he can use these stored software files to configure the camera to the appropriate settings for the type of testing. These settings files can be dated, so that the technician knows which file is most recent. The file can also be called up on the computing device in order to allow the technician to view and verify the settings when the file is called up for view on a screen of the computing device.

The software can also be configured to control image acquisition. However, if desired the technician can still manually acquire images using the camera. In an exemplary image acquisition, the technician can select the setting file, described above, acquire an image, and name that image to save it to a hard drive or networked drive of the computing device. After the image is named and saved, it can remain on the screen, such that the technician can complete various analysis tasks using the software.

For simple, efficient and effective image analysis purposes, the software can be configured to display a hard coded digital image scale, as illustrated in FIG. 9. The digital image scale can be superimposed over the acquired image, and the technician can also have the option of turning the digital image scale.

FIG. 10 illustrates an analysis tool, provided by the software control program for the device of the present invention. As illustrated in FIG. 10 the analysis tool can drop a circle 400 having a diameter of 10 pixels, at a point of interest in the image acquired using the device of the present invention. The pixel location of interest can also be recorded using the software control program, per requirements for various QA tasks. It should be noted that the diameter of the circle can be any number of pixels found suitable to one of skill in the art.

FIG. 11 illustrates a localization tool, provided by the software control program for the device of the present invention. As illustrated in FIG. 11 the localization tool can drop a first circle 500 having a diameter of 10 pixels. The localization tool then allows the technician to drag a line 502 to a second point of interest, where a second circle 504 can be dropped. In order to adjust the placement of the analysis tool, the line 502 can be stretched or shrunk. The software program can then be configured to determine and display the number of pixels defined by the line. If scale is available, the software program can be used to show the length of line 502 in mm.

FIG. 12 illustrates a region of interest tool, provided by the software program for the device of the present invention. The region of interest tool 600 can take the form of a square with crosshairs 602. Preferably, the region of interest tool 600 is 20 or more pixels in diameter depending on the camera resolution, to be roughly 5 mm. However, the region of interest tool can be configured to take any other suitable size known to or conceivable by one of skill in the art. The region of interest tool 600 can be a drag and drop tool, such that the technician can move it around to various regions of the image. Related tools could include an option to select pixels at the intersection of the crosshairs. Image statistics could also be calculated, such as mean pixel intensity and standard deviation. Additionally, the software can be configured to store user name and date on the image and also any specific information regarding pixel coordinates and statistics.

FIG. 13 illustrates an exemplary screen for defining scale in an acquired image taken using the device of the present invention. In the example, the technician acquires an optimal image 700 applies the digital image scale 702 described with respect to FIG. 9, and sets up a digital scale image. The technician can then call up a ruler tool to draw out a line 704. When the rule tool is called up, a dialog box can open, requesting a distance of the line in mm. The technician can confirm the distance, and the program calculates the scale in mm/pixel. The program can also be used to date and store the scale image. The scale created using this process is considered the default until it is remeasured and updated.

FIG. 14A illustrates an example of a program feature to superimpose images taken with the device of the present invention. A "superimpose" function key retrieves n number of images and superimposes the images on one another, as illustrated in FIG. 14A. More particularly, FIG. 14A illustrates an example with two laser images superimposed with a ruler image map. FIG. 14B illustrates an exemplary recording of laser QA to analyze the co-linearity of the laser, using the device of the present invention. If the lines of the laser in the image form a straight line, the medical accelerator receives a pass, but if they do not the medical accelerator receives a fail.

FIGS. 15-19 illustrate exemplary recordings of laser QA tasks executed with the device of the present invention. For instance, FIGS. 15 and 16A illustrate acquiring left and right lateral laser QA with the device of the present invention. The technician can select Laser QA tasks from a drop down menu. The Laser QA tasks list then includes options to perform QA for the left side of the room, the right side of the room, the ceiling of the room, and the back wall of the room. For left and right lateral QA, the program instructs the technician to acquire an image of a laser at the isocenter. The technician then localizes the laser crosshair using the pixel analysis tool described with respect to FIG. 10. The technician can then name and store the image. The technician is then prompted to acquire a second laser image after moving the treatment couch approximately 10 cm towards the laser. The technician then acquires a second image of the laser, and localizes the laser crosshair using the pixel analysis tool. This image is also named and stored. FIG. 16B illustrates an exemplary embodiment of the user interface showing the acquisition of a right room laser QA, as described with respect to FIG. 16A.

FIGS. 17 and 18 illustrate obtaining ceiling and back wall lateral laser QA, respectively, using the device of the present invention. In these examples, the technician acquires an image of the ceiling and the back wall lasers at isocenter. For FIG. 17, the technician localizes the laser cross-hairs and names and stores the ceiling laser image. The technician can then localize the intersection of the back wall and ceiling lasers, as illustrated in FIG. 18. The technician can then acquire another image after moving the treatment couch up toward the ceiling by 10 cm. The localization, naming, and storing procedures can be repeated for this image.

FIGS. 19 and 20 illustrate laser alignment analysis using the device of the present invention. The technician can request that the program perform laser analysis using the program menu. The program with combine isocenter locations for all laser crosshairs in a 2D or 3D view. The program will denote the lasers as a pass, if they are contained within a 2 mm diameter, as illustrated in FIG. 19. The program then derives co-linearity for each laser direction from the paired laser images, as illustrated in FIG. 20. The program will denote the lasers as a pass if the line is contained within a 2 mm diameter cylinder orthogonal to the isocenter over 20 cm.

Figure 21A:
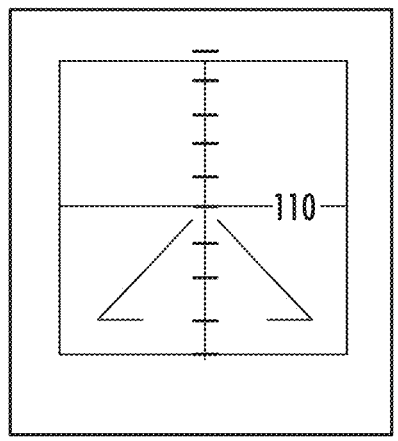
Figure 21B:
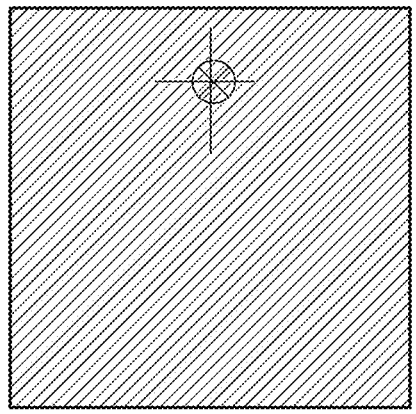
Figure 21C:
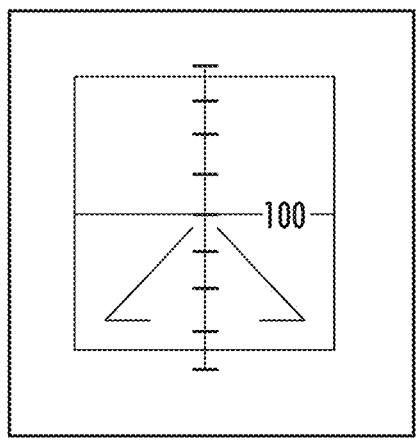
Figure 21D:
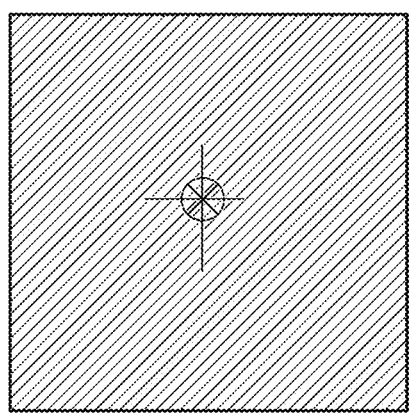
Figure 21E:
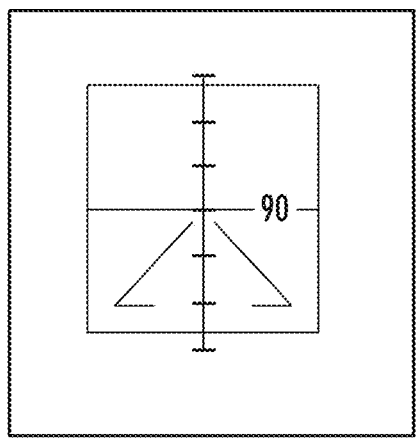
Figure 21F:
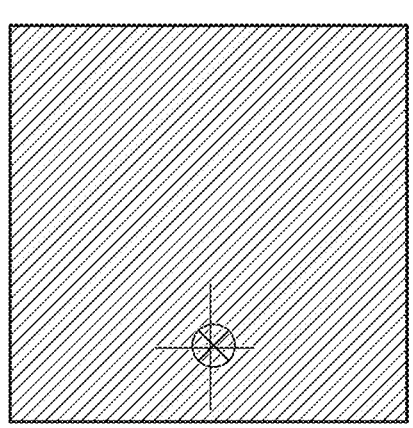

FIGS. 21A-F, 22A-F, and 23A-C illustrate exemplary recordings of table movement and optical distance indicator (ODI) QA tasks executed with the device of the present invention. FIGS. 21A-F relate to QA for table vertical movements captured using the device of the present invention. The program can be used to set the QA box to horizontal to acquire an ODI image at 110 cm SSD, as illustrated in FIG. 21A. The box can also be set manually and the images processed using the program. The QA box is then rotated vertical 90° to acquire a left or right laser image at 110 cm SSD as illustrated in FIG. 21B. This procedure is repeated for 100 cm SSD as illustrated in FIGS. 21C and 21D and 90 cm as illustrated in FIGS. 21E and 21F. The images can all be named and stored. The superimpose function, described above with respect to FIG. 14, can be used to measure vertical distance of the localized laser against the digital scale. The ruler tool can also be used. The program will denote this QA as a pass if the distance delta is within 1 mm.

Figure 22A:
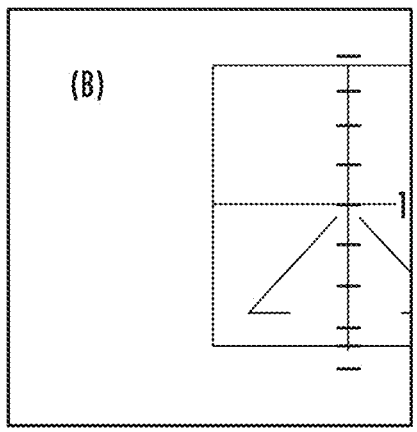
Figure 22B:
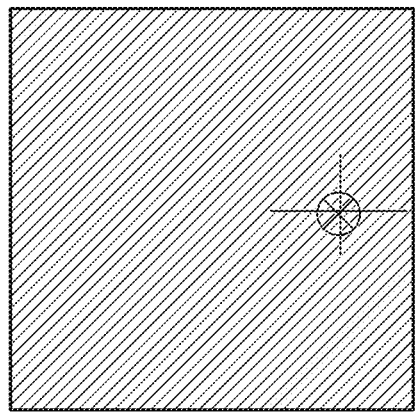
Figure 22C:
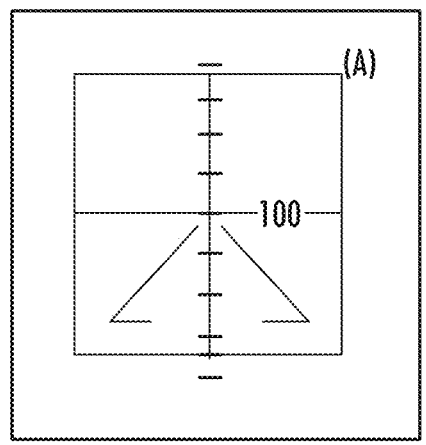
Figure 22D:
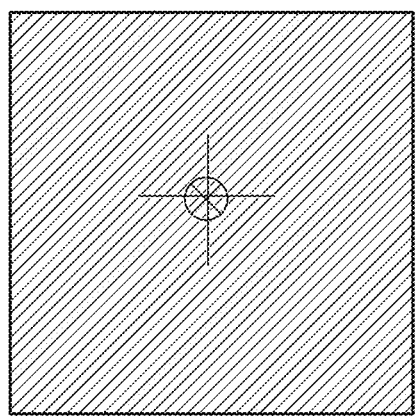
Figure 22E:
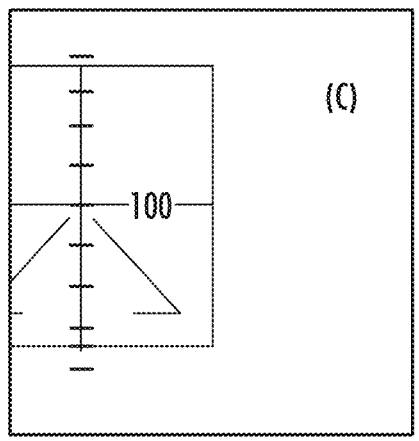
Figure 22F:
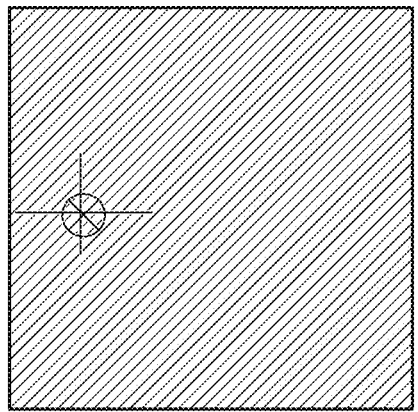
Figure 23A:
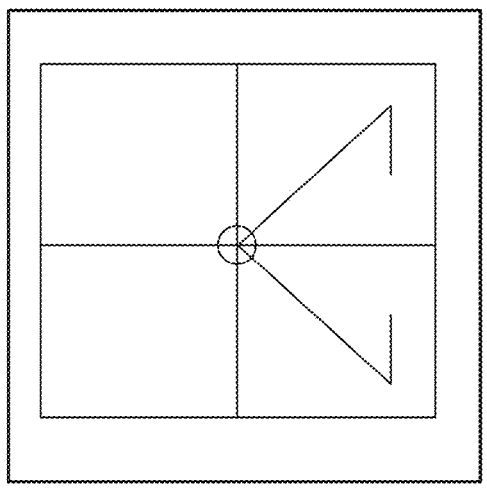
Figure 23B:
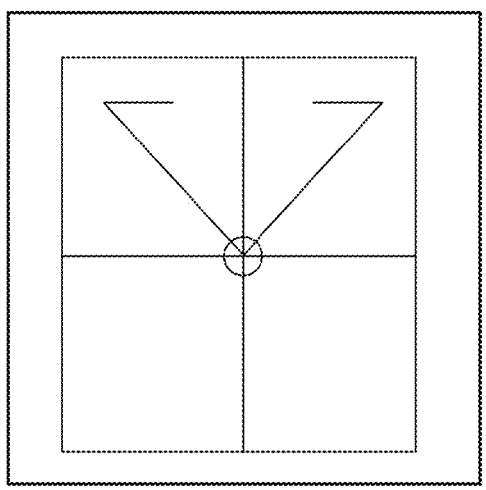
Figure 23C:
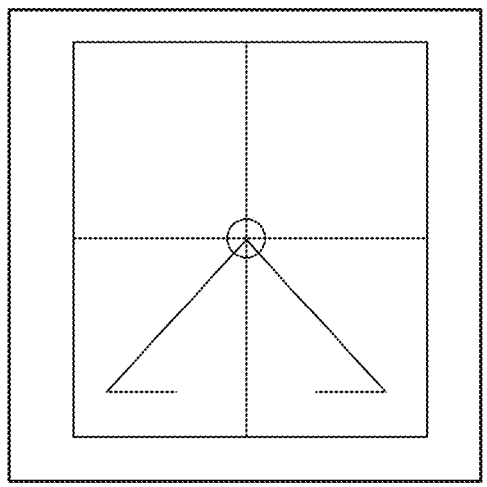
Figure 24A:
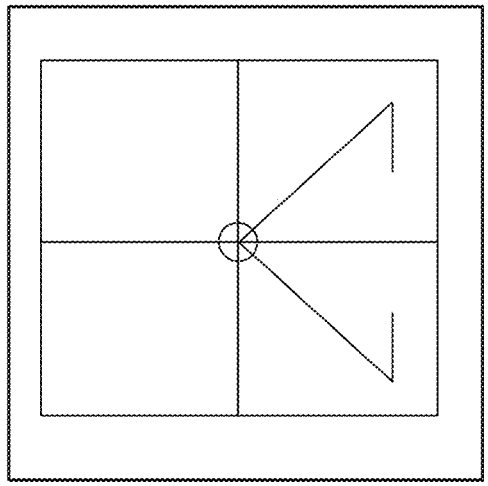
Figure 24B:
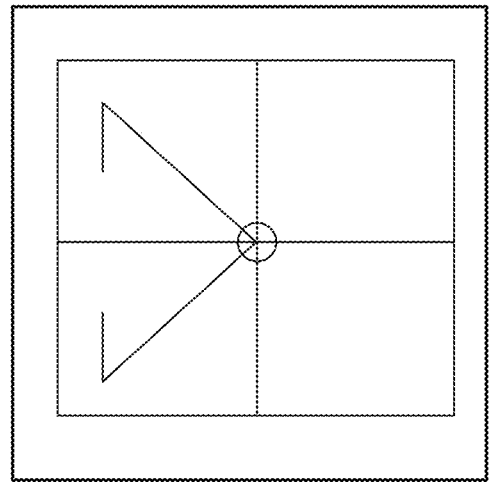
Figure 24C:
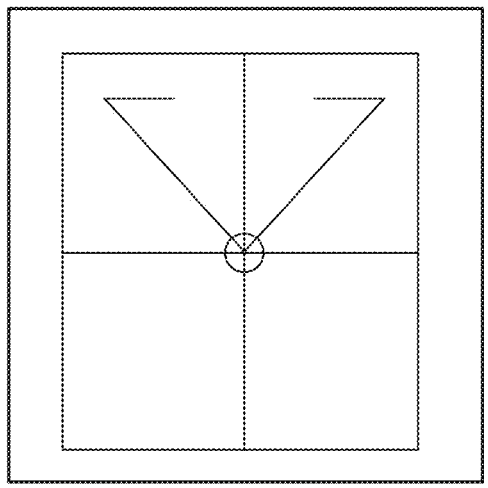
Figure 24D:
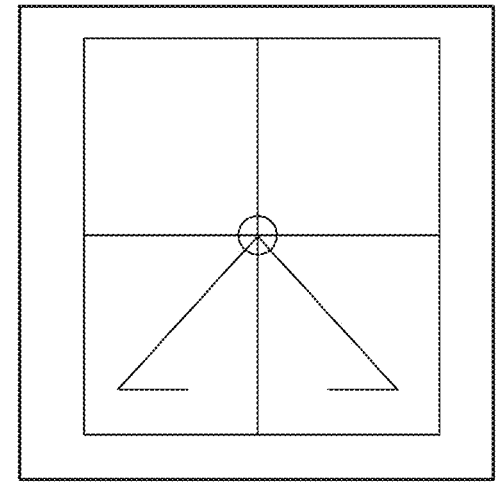

FIGS. 22A-F relate to QA for table lateral movements executed with the device of the present invention. The program can be used to set the QA box horizontal to acquire the optical field image at 100 cm SSD, as illustrated in FIG. 22A. The box can also be set manually and the images processed using the program. The technician also needs to acquire an image of the ceiling laser as illustrated in FIG. 22B. The procedures are repeated for a table move 10 cm to the left of center, as illustrated in FIGS. 22C and 22D and 10 cm to the right of center, as illustrated in FIGS. 22E and 22F. The superimpose function, described above with respect to FIG. 14, can be used to measure vertical distance of the localized laser against the digital scale. The ruler tool can also be used. The program will denote this QA as a pass if the distance delta is within 1 mm.

FIGS. 23A-C illustrates visual results of table rotation QA, using the device of the present invention. The QA box is set horizontal at the isocenter of the medical accelerator, either manually, or using the program. Optical images of the light field are acquired at table rotations of 180°, 90°, and 270°, as illustrated in FIGS. 23A-C, respectively, or any arbitrary but known angles. The crosshairs are localized in each image and the image is tagged and stored. The images can be superimposed using the feature discussed with respect to FIG. 14. The localized crosshairs must be within a circle of a 2 mm diameter in order for the system to pass this QA analysis.

As illustrated in FIGS. 24A-D collimator rotation QA is executed in much the same manner as table rotation QA, using the device of the present invention. The QA box is set horizontal at the isocenter of the medical accelerator, either manually, or using the program. Optical images of the light field are acquired at collimator rotations of 180°, 0°, 90°, and 270°, as illustrated in FIGS. 24A-D, respectively, or any arbitrary but known angles. The crosshairs are localized in each image and the image is tagged and stored. The images can be superimposed using the feature discussed with respect to FIG. 14. The localized crosshairs must be within a circle of a 2 mm diameter in order for the system to pass this QA analysis.

FIGS. 25A-D, 26, 27A and 27B, and 28A and 28B illustrate the visual results of radiation and light field congruence QA, using the device of the present invention. For general radiation field acquisition, which can be executed manually or using the device control program, the radiation camera setting is selected to acquire dark current image with the camera shut for 15 sec or 3×15 sec. Radiation exposure is acquired for the same exposure setting and camera-lens non-uniformity correction is applied if applicable. A mean dark current image can be subtracted from the "corrected" mean radiation image.

Particularly, as illustrated in FIGS. 25A-25D a radiation/light field congruence tool can be used to produce images similar to the examples shown in FIGS. 25A and 25B. The optical camera setting is selected either manually or using the device control program, in order to acquire a light field at preset dimensions, such as 20 cm×20 cm. A previously stored image can also be used. The program can then be used to detect a light field boundary. The radiation camera setting is used to acquire and process dark current and a radiation field for the same dimensions. Radiation field boundary can then be detected at an intensity level of 50%. The light field boundary and the radiation field boundary can then be overlaid and the image named and stored. FIG. 25C illustrates an exemplary embodiment of the user interface showing the acquisition of a 6 MV x-ray QA, as described with respect to FIGS. 25A and 25B. FIG. 25D illustrates another example of a light field and radiation field congruence image acquired using the device of the present invention.

FIG. 26 illustrates a graph obtained using a profile tool in the control program for the device of the present invention. In order to use the profile tool a radiation image must be obtained. The program can then be asked to display a 1D plot of x- or y-profiles, such as the graph of FIG. 26. The light field boundaries 600 can also be displayed on the graph. The graph can be used to calculate flatness, symmetry, and uniformity index according to formulae. The graph and results can be stored for future reference.

FIGS. 27A and 27B illustrate exemplary plots to show calculation methods for determining photon beam flatness and symmetry using a 1D plot, like the one illustrated in FIG. 26. The photon beam flatness (F) calculation is illustrated in FIG. 27A, where $F=100*(D_{max}-D_{min})/D_{max}+D_{min})$. The symmetry (S) calculation is illustrated in FIG. 27B, where $S=100*(area_{left}-area_{right})/(area_{left}+area_{right})$. The graph and results can be stored for future reference.

FIGS. 28A and 28B illustrate visual representations of radiation measurements taken using the device of the present invention. FIG. 28A illustrates a visual representation of the radiation field, and FIG. 28B illustrates a calculation of the uniformity index (UI), where $UI=area_{90}\%)/(area_{50}\%)$. The graph and results can be stored for future reference.

FIG. 29 and FIGS. 30A and 30B illustrate visual representations of radiation field acquisition and analysis. It should be noted that when radiation fields are imaged using the device of the present system, a simultaneous film measurement can also be taken. The ratio of the film measurement to the measurement from the camera of the device of the present invention can then be used to provide a one-time correction map that can be used for every test measurement. More particularly, FIG. 29 illustrates a visual representation of a mean radiation image, taken using the device of the present invention. The device can measure any radiation field such as 4, 6, 8, 10, 15, or 18 MV x-rays or 6, 8, 1-, 12, 15, and 18 MeV electron beams. Dark current and radiation images are acquired according to the protocols described above. The images are then processed by the program to create a mean radiation image. The image can be named and stored for further reference or additional calculations such as flatness, symmetry and uniformity index, all described previously.

FIGS. 30A and 30B illustrate exemplary visual representations of energy checks for radiation analysis. To perform the energy checks the technician acquires a pair of appropriate mean radiation images taken under different thicknesses of a material such as plastic or simulated solid water. A region of interest is placed at a center of the radiation image such as Reading 1 (R1) and Reading 2 (R2) in FIGS. 30A and 30B. R1=the average count for the region of interest for the first image, and R2=the average count for the region of interest for the second image. The energy constant ratio=R1/R2. These results can also be named and stored for future use or reference.

FIGS. 31, 32A-B, and 33A-B illustrate visual representations and analysis of multi-leaf collimator (MLC) QA measurements, taken using a device of the present invention. These analyses ensure MLC positioning accuracy using garden fence delivery, and leaf speed accuracy. With respect to FIGS. 31 and 32A-B, which illustrate visual representation of garden fence analyses, a garden fence image is acquired by setting an integration camera time to 30 sec or more. Imaging begins and the technician drives a slit beam, formed by X1, X2 MLC in the step and shoot mode to deliver radiation to known positions in the field. After delivery and imaging is stopped the positional accuracy of the leaf gap can be analyzed, as in FIGS. 31, and 32A-B.

FIGS. 33A and 33B illustrate visual representations of measurement and analysis for leaf speed of the MLC. An image is acquired by setting an integration camera time to 30 sec or more. Imaging begins and the technician drives each leaf pair with different speeds across the field to deliver different doses for each leaf pair. After delivery and imaging is stopped the positional accuracy of the dose profile can be analyzed, as in FIGS. 33A-B.

The above described software tools for automating the QA process and analyzing the images taken with the device of the present invention are exemplary and are not to be considered limiting. Many other software tools could be developed to further automate the process and provide for analysis of the images. The control program for the present invention can also be configured to produce a report outlining all of the QA measurements executed and the results of those measurements.

FIG. 34 illustrates an ion chamber for use with a device for QA of a medical accelerator, according to an embodiment of the present invention. The ion chamber 800 can take the form of sheets of plastic water 802 positioned on a surface of the device 804. The sheets of plastic water 802 can be up to 10 cm thick. Additionally, one sheet can include a receptor 806 for an ion chamber 808. (There are no numbering in the Figure) The receptor 808 can be drilled at a 45° angle to a x-y axis of the chamber 800. This configuration allows for TG51 calibration to be performed.

A method in accordance with the present invention includes using a QA device of the present invention, described above, to assess the integrity of collimator rotation. The method includes setting the QA device flat at the isocenter of the collimator and/or the couch. Preferably, the QA device is positioned such that the QA device is hanging off an end of the couch. A small square field of approximately 2 cm×2 cm, or any other suitable field size known to or conceivable by one of skill in the art, is set up. The QA device is exposed to a radiation field with the collimator at an angle. The exposure to radiation field is repeated for various collimator angles. A center of mass of all of the radiation fields imaged by the QA device gives a measure of the isocenter integrity of collimator rotation. FIG. 35 illustrates an exemplary exposure of the QA device at an angle of collimator rotation in order to assess integrity of collimator rotation, and also an exemplary range of rotation of the collimator disposed around the exemplary exposure. The center of mass can be analyzed digitally using a computer, table computing device, smart phone, server, or any other suitable digital processing unit or computing device. Alternately the center of mass can be analyzed manually.

Another method in accordance with the present invention includes using a QA device of the present invention, described above, to assess the integrity of gantry rotation. The method includes setting the QA device flat at the isocenter of the gantry and/or the couch. Preferably, the QA device is positioned such that it hangs off of an end of the couch. A small square field of approximately 2 cm×2 cm, or any other suitable field size known to or conceivable by one of skill in the art, is set up. The QA device is exposed to the radiation field with the gantry angled at +/−60° above the QA device. A square radiation field image will become rectangular at certain gantry angles. The box can then be rotated 90°, 180°, and 270°. The center of mass of all of the radiation fields will give a measure of the integrity of the isocenter of the gantry rotation in a top half of the gantry space. The center of mass can be analyzed digitally using a computer, table computing device, smart phone, server, or any other suitable digital processing unit or computing device. Alternately the center of mass can be analyzed manually. FIG. 36A illustrates an exemplary exposure of the QA device at a 0° angle of gantry rotation in order to assess integrity of gantry rotation. FIG. 36B illustrates an exemplary exposure of the QA device at a 30° angle of gantry rotation in order to assess integrity of gantry rotation.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A method for real-time mechanical and dosimetric quality assurance measurements in radiation therapy, comprising:
    positioning a QA device at an isocenter of a medical accelerator;
    setting up a small square radiation field;
    exposing the QA device to the small square radiation field at an angle of the collimator;
    repeating the exposure to the small square radiation field is repeated for various collimator angles;
    determining a center of mass of all of the small square radiation fields imaged by the QA device to obtain a measure of the isocenter integrity of collimator rotation.

2. The method of claim 1 further comprising positioning the QA device on a couch of the medical accelerator.

3. The method of claim 1 wherein the isocenter is an isocenter of at least one selected from the group of collimator or couch.

4. The method of claim 1 further comprising positioning the QA device such that the QA device is hanging off an end of the couch.

5. The method of claim 1 wherein the radiation field is approximately 2 cm×2 cm.

6. The method of claim 1 further comprising using a computing device to determine the center of mass of all of the small square radiation fields to obtain the measure of isocenter integrity.

7. A method for real-time mechanical and dosimetric quality assurance measurements in radiation therapy, comprising:
    positioning a QA device at an isocenter of a medical accelerator;
    setting up a small square radiation field;
    exposing the QA device to the small square radiation field at an angle of the gantry;
    rotating the QA device;
    repeating the exposure to the small square radiation field;
    determining a center of mass of all of the small square radiation fields imaged by the QA device to obtain a measure of the isocenter integrity of gantry rotation.

8. The method of claim 7 further comprising positioning the QA device on a couch of the medical accelerator.

9. The method of claim 7 wherein the isocenter is an isocenter of at least one selected from the group of gantry or couch.

10. The method of claim 7 further comprising positioning the QA device such that the QA device is hanging off an end of the couch.

11. The method of claim 7 wherein the radiation field is approximately 2 cm×2 cm.

12. The method of claim 7 further comprising using a computing device to determine the center of mass of all of the small square radiation fields to obtain the measure of isocenter integrity.

13. The method of claim 7 further comprising rotating the QA device such that it is at 0°, 90°, 180°, and 270° from an original position of the box.

14. The method of claim 7 further comprising rotating the gantry between approximately +/−60°.

\* \* \* \* \*